(12) United States Patent
Patient et al.

(10) Patent No.: US 11,530,208 B2
(45) Date of Patent: *Dec. 20, 2022

(54) IMIDAZO[4,5-C]PYRIDINE DERIVED SSAO INHIBITORS

(71) Applicant: PROXIMAGEN, LLC, Plymouth, MN (US)

(72) Inventors: Lee Patient, Linton (GB); Iain Simpson, Cambridge (GB); Edward Savory, Cambourne (GB)

(73) Assignee: PROXIMAGEN, LLC, Plymouth, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/506,847

(22) PCT Filed: Sep. 17, 2015

(86) PCT No.: PCT/GB2015/052691
§ 371 (c)(1),
(2) Date: Feb. 27, 2017

(87) PCT Pub. No.: WO2016/042332
PCT Pub. Date: Mar. 24, 2016

(65) Prior Publication Data
US 2017/0275281 A1    Sep. 28, 2017

(30) Foreign Application Priority Data

Sep. 17, 2014    (GB) .................................... 1416444

(51) Int. Cl.
| C07D 471/04 | (2006.01) |
| C07D 403/04 | (2006.01) |
| C07D 403/14 | (2006.01) |
| A61K 31/436 | (2006.01) |
| A61K 31/437 | (2006.01) |

(52) U.S. Cl.
CPC .......... C07D 471/04 (2013.01); A61K 31/436 (2013.01); A61K 31/437 (2013.01); C07D 403/04 (2013.01); C07D 403/14 (2013.01)

(58) Field of Classification Search
CPC .. C07D 471/04; C07D 403/04; A61K 31/436; A61K 31/437
USPC ........................................................ 546/118
See application file for complete search history.

(56) References Cited

U.S. PATENT DOCUMENTS

| 7,405,300 | B2 | 7/2008 | Jiang et al. | |
| 9,428,498 | B2* | 8/2016 | Espensen | A61P 25/28 |
| 9,580,415 | B2 | 2/2017 | Patient et al. | |
| 9,676,769 | B2* | 6/2017 | Espensen | C07D 471/04 |
| 9,951,068 | B2* | 4/2018 | Espensen | C07D 471/04 |
| 10,428,066 | B2* | 10/2019 | Espensen | A61K 31/501 |
| 10,590,125 | B2* | 3/2020 | Espensen | C07D 471/04 |

| 2005/0054631 | A1 | 3/2005 | Jiang et al. | |
| 2012/0095037 | A1 | 4/2012 | Winfield | |
| 2014/0275040 | A1 | 9/2014 | Espensen et al. | |
| 2015/0258101 | A1* | 9/2015 | Espensen | A61K 31/5377 514/234.2 |
| 2016/0024080 | A1 | 1/2016 | Patient et al. | |
| 2016/0046622 | A1 | 2/2016 | Espensen et al. | |
| 2016/0326172 | A1 | 11/2016 | Espensen et al. | |

FOREIGN PATENT DOCUMENTS

| WO | 2002038153 A1 | 5/2002 | |
| WO | 2003006003 A1 | 1/2003 | |
| WO | 2005014530 A | 2/2005 | |
| WO | 2007120528 A2 | 10/2007 | |
| WO | 2010031789 A1 | 3/2010 | |
| WO | 2010031791 A1 | 3/2010 | |
| WO | 2010064020 A1 | 6/2010 | |
| WO | 2010117935 A1 | 10/2010 | |
| WO | 2011113798 A2 | 9/2011 | |
| WO | WO2012146667 | * 11/2012 | ........... C07D 473/34 |
| WO | WO-2012146667 A1 | * 11/2012 | ............... A61P 9/00 |
| WO | 2013037411 A1 | 3/2013 | |
| WO | 2013038189 A1 | 3/2013 | |
| WO | 2013078254 A1 | 5/2013 | |
| WO | 2014140591 A1 | 9/2014 | |
| WO | 2014140592 A1 | 9/2014 | |
| WO | WO-2014140592 A1 | * 9/2014 | ........... C07D 471/04 |
| WO | 2015189534 A1 | 12/2015 | |

(Continued)

OTHER PUBLICATIONS

Kamila Sukanta et al, Synthesis of Novel Pyrido Pyridobenzimidazoles Bonded to Indoleorbenzo[b]thiophenestructures (Year: 2011).*
Heidi Schilter et al, Effects of an anti-inflammatory VAP-SSAP inhibitor, PXS-4728A on pulmonary neutrophil migration. (Year: 2015).*
English abstract, Caplus Yutilov Yu 1975, 2-Aldehydes . (Year: 1975).*

(Continued)

*Primary Examiner* — John S Kenyon
(74) *Attorney, Agent, or Firm* — Ballard Spahr LLP

(57) ABSTRACT

A compound of formula (I) or a pharmaceutically acceptable salt, or N-oxide thereof and the use of the same in therapy: wherein Z, Y, $R^1$, W, V, and $R^3$ are as defined in claim 1.

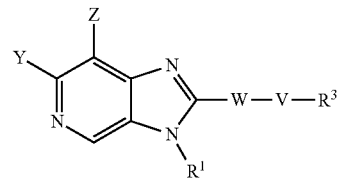

(I)

16 Claims, No Drawings

(56) References Cited

FOREIGN PATENT DOCUMENTS

| WO | 2016042331 A1 | 3/2016 | | |
|---|---|---|---|---|
| WO | WO-2017098236 A1 | * | 6/2017 | ............ A61K 31/137 |
| WO | WO-2018224837 A1 | * | 12/2018 | ............ A61K 31/121 |

OTHER PUBLICATIONS

Marko Salmi et al. Vascular adhesion Protein-1: A cell surface Amine Oxidase in Translation. (Year: 2019).*
CAS Registry No. 340159-15-1, Jun. 8, 2001, Compound 2-(2,3-dihydro-1,3-dimethyl-1H-benzimidazol-2-yl)-3-phenyl-3H-imidazo[4,5-c]pyridine.
Database Registry [online], Chemical Abstracts Service, Columbus, Ohio, US; Jan. 19, 2011, XP002723294, database accession No. 1259952-23-2 abstract.
Dunkel, Petra et al. "Semicarbazide-sensitive amine oxidase/vascular adhesion protein-1: a patent survey," Expert Opin. Ther. Patents, 21(9): 1453-1471 (2011).
International Search Report dated Dec. 15, 2015 for PCT application No. PCT/GB2015/052690 filed Sep. 17, 2015.
International Search Report dated Dec. 15, 2015 for PCT application No. PCT/GB2015/052691 filed Sep. 17, 2015.
Melkonyan, Ferdinand S., et al. "One-pot synthesis of substituted indoles via titanium(iv) alkoxide mediated imine formation—copper-catalyzed N-arylation," RSC Advances, vol. 3, No. 22, Mar. 21, 2013, p. 8388, XP055113497.
UKIPO Search Report dated Jan. 13, 2016 for GB Application No. 1416444.6 filed on Sep. 17, 2014.
Wilson, Robert J., et al. "Copper- and Palladium-Catalyzed Amidation Reactions for the Synthesis of Substituted Imidazo[4,5-c]pyridines," The Journal of Organic Chemistry, vol. 79, No. 5, Feb. 6, 2014, pp. 2203-2212, XP055113503.
V. Craig Jordan, 2 Nature Reviews 205 (2003).
Daniel G. Hackam and Donald A. Redelmeier 296 JAMA 1731 (2006).
Search Report dated Aug. 22, 2013 for GB Application No. 1304526.5 filed Mar. 13, 2013.
International Search Report dated Apr. 28, 2014 for PCT Application No. PCT/GB2014/050764 filed Mar. 13, 2014.
International Search Report dated May 8, 2014 for PCT Application No. PCT/GB2014/050765 filed Mar. 13, 2014.
Notice of Allowance dated Jun. 24, 2015, in co-pending U.S. Appl. No. 14/208,056 (U.S. Publication No. 2014/0275040) filed Mar. 13, 2016 now U.S. Pat. No. 9,428,498.
Search Report dated Aug. 28, 2013 from GB Application No. 1304527.3 filed Mar. 13, 2013.

* cited by examiner

IMIDAZO[4,5-C]PYRIDINE DERIVED SSAO INHIBITORS

This application is a 371 national stage application of international patent application no. PCT/GB2015/052691 filed on Sep. 17, 2015, which claims priority to United Kingdom application number 1416444.6 filed on Sep. 17, 2014. The above applications are incorporated herein by reference in their entirety.

FIELD OF THE INVENTION

The present invention relates to compounds which are inhibitors of SSAO activity. The invention also relates to pharmaceutical compositions comprising these compounds and to the use of these compounds in the treatment or prevention of medical conditions wherein inhibition of SSAO activity is beneficial, such as inflammatory diseases, immune disorders and the inhibition of tumour growth.

BACKGROUND ART

Semicarbazide-sensitive amine oxidase (SSAO) activity is an enzyme activity expressed by Vascular Adhesion Protein-1 (VAP-1) or Amine Oxidase, Copper Containing 3 (AOC3), belongs to the copper-containing amine oxidase family of enzymes (EC.1.4.3.6). Therefore inhibitors of the SSAO enzyme may also modulate the biological functions of the VAP-1 protein. Members of this enzyme family are sensitive to inhibition by semicarbazide and utilize cupric ion and protein-derived topa quinone (TPQ) cofactor in the oxidative deamination of primary amines to aldehydes, hydrogen peroxide, and ammonia according to the following reaction:

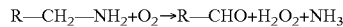

$$R-CH_2-NH_2+O_2 \rightarrow R-CHO+H_2O_2+NH_3$$

Known substrates for human SSAO include endogenous methylamine and aminoacetone as well as some xenobiotic amines such as benzylamine [Lyles, *Int. J. Biochem. Cell Biol.* 1996, 28, 259-274; Klinman, *Biochim. Biophys. Acta* 2003, 1647(1-2), 131-137; Mátyus et al., *Curr. Med. Chem.* 2004, 11(10), 1285-1298; O'Sullivan et al., *Neurotoxicology* 2004, 25(1-2), 303-315]. In analogy with other copper-containing amine oxidases, DNA-sequence analysis and structure determination suggest that the tissue-bound human SSAO is a homodimeric glycoprotein consisting of two 90-100 kDa subunits anchored to the plasma membrane by a single N-terminal membrane spanning domain [Morris et al., *J. Biol. Chem.* 1997, 272, 9388-9392; Smith et al., *J. Exp. Med.* 1998, 188, 17-27; Airenne et al., *Protein Science* 2005, 14, 1964-1974; Jakobsson et al., *Acta Crystallogr. D Biol. Crystallogr.* 2005, 61(Pt 11), 1550-1562].

SSAO activity has been found in a variety of tissues including vascular and non-vascular smooth muscle tissue, endothelium, and adipose tissue [Lewinsohn, *Braz. J. Med. Biol. Res.* 1984, 17, 223-256; Nakos & Gossrau, *Folia Histochem. Cytobiol.* 1994, 32, 3-10; Yu et al., *Biochem. Pharmacol.* 1994, 47, 1055-1059; Castillo et al., *Neurochem. Int.* 1998, 33, 415-423; Lyles & Pino, *J. Neural. Transm. Suppl.* 1998, 52, 239-250; Jaakkola et al., *Am. J. Pathol.* 1999, 155, 1953-1965; Morin et al., *J. Pharmacol. Exp. Ther.* 2001, 297, 563-572; Salmi & Jalkanen, *Trends Immunol.* 2001, 22, 211-216]. In addition, SSAO protein is found in blood plasma and this soluble form appears to have similar properties as the tissue-bound form [Yu et al., *Biochem. Pharmacol.* 1994, 47, 1055-1059; Kurkijärvi et al., *J. Immunol.* 1998, 161, 1549-1557]. It has recently been shown that circulating human and rodent SSAO originates from the tissue-bound form [Göktürk et al., *Am. J. Pathol.* 2003, 163(5), 1921-1928; Abella et al., *Diabetologia* 2004, 47(3), 429-438; Stolen et al., *Circ. Res.* 2004, 95(1), 50-57], whereas in other mammals the plasma/serum SSAO is also encoded by a separate gene called AOC4 [Schwelberger, *J. Neural. Transm.* 2007, 114(6), 757-762].

The precise physiological role of this abundant enzyme has yet to be fully determined, but it appears that SSAO and its reaction products may have several functions in cell signalling and regulation. For example, recent findings suggest that SSAO plays a role in both GLUT4-mediated glucose uptake [Enrique-Tarancon et al., *J. Biol. Chem.* 1998, 273, 8025-8032; Morin et al., *J. Pharmacol. Exp. Ther.* 2001, 297, 563-572] and adipocyte differentiation [Fontana et al., *Biochem. J.* 2001, 356, 769-777; Mercier et al., *Biochem. J.* 2001, 358, 335-342]. In addition, SSAO has been shown to be involved in inflammatory processes where it acts as an adhesion protein for leukocytes [Salmi & Jalkanen, *Trends Immunol.* 2001, 22, 211-216; Salmi & Jalkanen, in "*Adhesion Molecules: Functions and Inhibition*" K. Ley (Ed.), 2007, pp. 237-251], and might also play a role in connective tissue matrix development and maintenance [Langford et al., *Cardiovasc. Toxicol.* 2002, 2(2), 141-150; Göktürk et al., *Am. J. Pathol.* 2003, 163(5), 1921-1928]. Moreover, a link between SSAO and angiogenesis has recently been discovered [Noda et al., *FASEB J.* 2008, 22(8), 2928-2935], and based on this link it is expected that inhibitors of SSAO have an anti-angiogenic effect.

Several studies in humans have demonstrated that SSAO activity in blood plasma is elevated in conditions such as congestive heart failure, diabetes mellitus, Alzheimer's disease, and inflammation [Lewinsohn, *Braz. J. Med. Biol. Res.* 1984, 17, 223-256; Boomsma et al., *Cardiovasc. Res.* 1997, 33, 387-391; Ekblom, *Pharmacol. Res.* 1998, 37, 87-92; Kurkijärvi et al., *J. Immunol.* 1998, 161, 1549-1557; Boomsma et al., *Diabetologia* 1999, 42, 233-237; Meszaros et al., *Eur. J. Drug Metab. Pharmacokinet.* 1999, 24, 299-302; Yu et al., *Biochim. Biophys. Acta* 2003, 1647(1-2), 193-199; Mátyus et al., *Curr. Med. Chem.* 2004, 11(10), 1285-1298; O'Sullivan et al., *Neurotoxicology* 2004, 25(1-2), 303-315; del Mar Hernandez et al., *Neurosci. Lett.* 2005, 384(1-2), 183-187]. The mechanisms underlying these alterations of enzyme activity are not clear. It has been suggested that reactive aldehydes and hydrogen peroxide produced by endogenous amine oxidases contribute to the progression of cardiovascular diseases, diabetic complications and Alzheimer's disease [Callingham et al., *Prog. Brain Res.* 1995, 106, 305-321; Ekblom, *Pharmacol. Res.* 1998, 37, 87-92; Yu et al., *Biochim. Biophys. Acta* 2003, 1647(1-2), 193-199; Jiang et al., *Neuropathol Appl Neurobiol.* 2008, 34(2), 194-204]. Furthermore, the enzymatic activity of SSAO is involved in the leukocyte extravasation process at sites of inflammation where SSAO has been shown to be strongly expressed on the vascular endothelium [Salmi et al., *Immunity* 2001, 14(3), 265-276; Salmi & Jalkanen, in "*Adhesion Molecules: Functions and Inhibition*" K. Ley (Ed.), 2007, pp. 237-251]. Accordingly, inhibition of SSAO has been suggested to have a therapeutic value in the prevention of diabetic complications and in inflammatory diseases [Ekblom, *Pharmacol. Res.* 1998, 37, 87-92; Salmi et al., *Immunity* 2001, 14(3), 265-276; Salter-Cid et al., *J. Pharmacol. Exp. Ther.* 2005, 315(2), 553-562].

WO2007146188 teaches that blocking SSAO activity inhibits leucocyte recruitment, reduces the inflammatory response, and is expected to be beneficial in prevention and treatment of seizures, for example, in epilepsy.

O'Rourke et al (J Neural Transm. 2007; 114(6):845-9) examined the potential of SSAO inhibitors in neurological diseases, having previously demonstrated the efficacy of SSAO inhibition in a rat model of stroke. An SSAO inhibitor is tested on relapsing-remitting experimental autoimmune encephalomyelitis (EAE), a mouse model that shares many characteristics with human multiple sclerosis. The data demonstrates the potential clinical benefit of small molecule anti-SSAO therapy in this model and therefore in treatment of human multiple sclerosis.

SSAO knockout animals are phenotypically overtly normal but exhibit a marked decrease in the inflammatory responses evoked in response to various inflammatory stimuli [Stolen et al., *Immunity* 2005, 22(1), 105-115]. In addition, antagonism of its function in wild type animals in multiple animal models of human disease (e.g. carrageenan-induced paw inflammation, oxazolone-induced colitis, lipopolysaccharide-induced lung inflammation, collagen-induced arthritis, endotoxin-induced uveitis) by the use of antibodies and/or small molecules has been shown to be protective in decreasing the leukocyte infiltration, reducing the severity of the disease phenotype and reducing levels of inflammatory cytokines and chemokines [Kirton et al., *Eur. J. Immunol.* 2005, 35(11), 3119-3130; Salter-Cid et al., *J. Pharmacol. Exp. Ther.* 2005, 315(2), 553-562; McDonald et al., *Annual Reports in Medicinal Chemistry* 2007, 42, 229-243; Salmi & Jalkanen, in "*Adhesion Molecules: Functions and Inhibition*" K. Ley (Ed.), 2007, pp. 237-251; Noda et al., *FASEB J.* 2008 22(4), 1094-1103; Noda et al., *FASEB J.* 2008, 22(8), 2928-2935]. This anti-inflammatory protection seems to be afforded across a wide range of inflammatory models all with independent causative mechanisms, rather than being restricted to one particular disease or disease model. This would suggest that SSAO may be a key nodal point for the regulation of the inflammatory response, and it is therefore likely that SSAO inhibitors will be effective anti-inflammatory drugs in a wide range of human diseases. VAP-1 has also been implicated in the progression and maintenance of fibrotic diseases including those of the liver and lung. Weston and Adams (J Neural Transm. 2011, 118(7), 1055-64) have summarised the experimental data implicating VAP-1 in liver fibrosis, and Weston et al (EASL Poster 2010) reported that blockade of VAP-1 accelerated the resolution of carbon tetrachloride induced fibrosis. In addition VAP-1 has been implicated in inflammation of the lung (e.g. Singh et al., 2003, Virchows Arch 442:491-495) suggesting that VAP-1 blockers would reduce lung inflammation and thus be of benefit to the treatment of cystic fibrosis by treating both the pro-fibrotic and pro-inflammatory aspects of the disease.

SSAO (VAP-1) is up regulated in gastric cancer and has been identified in the tumour vasculature of human melanoma, hepatoma and head and neck tumours (Yoong K F, McNab G, Hubscher S G, Adams D H. (1998), J Immunol 160, 3978-88; Irjala H, Salmi M, Alanen K, Gre'nman R, Jalkanen S (2001), Immunol. 166, 6937-6943; Forster-Horvath C, Dome B, Paku S, et al. (2004), Melanoma Res. 14, 135-40.). One report (Marttila-Ichihara F, Castermans K, Auvinen K, Oude Egbrink M G, Jalkanen S, Griffioen A W, Salmi M. (2010), J Immunol. 184, 3164-3173) has shown that mice bearing enzymically inactive VAP-1 grow melanomas more slowly, and have reduced tumour blood vessel number and diameter. The reduced growth of these tumours was also reflected in the reduced (by 60-70%) infiltration of myeloid suppressor cells. Encouragingly VAP-1 deficiency had no effect on vessel or lymph formation in normal tissue.

Small molecules of different structural classes have previously been disclosed as SSAO inhibitors, for example in WO 02/38153 (tetrahydroimidazo[4,5-c]pyridine derivatives), in WO 03/006003 (2-indanylhydrazine derivatives), in WO 2005/014530 (allylhydrazine and hydroxylamine (aminooxy) compounds) and in WO 2007/120528 (allylamino compounds). Additional SSAO inhibitors are disclosed in WO2013/037411 and WO2013/038189.

Patent application PCT/US2012/066153 (published as WO2013/078254) discloses compounds apparently useful as inhibitors of serine/threonine protein kinases. The compounds disclosed therein have a bicyclic heteroaryl ring system substituted with a phenyl-cyclobutaneamine substituent.

The invention described here relates to a new class of SSAO inhibitors with biological, pharmacological, and pharmacokinetic characteristics that make them suitable for use as prophylactic or therapeutic agents in a wide range of human inflammatory diseases and immune disorders. This therapeutic capacity is designed to block SSAO enzyme action, reducing the levels of pro-inflammatory enzyme products (aldehydes, hydrogen peroxide and ammonia) whilst also decreasing the adhesive capacity of immune cells and correspondingly their activation and final extra-vasation. Diseases where such an activity is expected to be therapeutically beneficial include all diseases where immune cells play a prominent role in the initiation, maintenance or resolution of the pathology, such as multiple sclerosis, arthritis and vasculitis.

Our co-pending International Patent Application No. PCT/GB2014/050765 relates to SSAO inhibitors of formula (I) or a pharmaceutically acceptable salt, or N-oxide thereof:

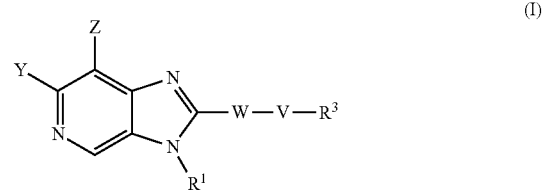

(I)

Wherein:

Y is selected from hydrogen, hydroxyl, —NH$_2$, —NH—C$_{1-4}$-alkyl, —NH-halo-C$_{1-4}$-alkyl, or —C$_{1-4}$-alkoxy;

Z is selected from hydrogen, halogen, hydroxyl, cyano, C$_{1-4}$-alkyl, halo-C$_{1-4}$-alkyl, C$_{1-4}$-alkoxy, halo-C$_{1-4}$-alkoxy, —CONH$_2$, —SO$_2$NH$_2$, —NH$_2$, —NHC$_{1-4}$-alkyl, or —NHhalo-C$_{1-4}$-alkyl;

R$^1$ is a phenyl ring, or a 5 or 6-membered heteroaryl ring, either ring being optionally substituted with one or more substituents selected from halogen, cyano, C$_{1-4}$-alkyl, halo-C$_{1-4}$-alkyl, cyano-C$_{1-4}$-alkyl, a 3-7 membered cycloalkyl ring, —OR$^5$, —NR$^{4A}$R$^{4B}$, —NR$^6$C(O)OR$^5$, —NR$^6$C(O)R$^5$, —NR$^6$C(O)NR$^{4A}$R$^{4B}$, —C(O)NR$^{4A}$R$^{4B}$, —C(O)R$^5$, —C(O)OR$^5$, and —NR$^6$S(O)$_2$R$^5$; wherein R$^{4A}$, R$^{4B}$ R$^5$ and R$^6$ are each independently selected from hydrogen, C$_{1-4}$-alkyl or halo-C$_{1-4}$-alkyl, or R$^{4A}$ and R$^{4B}$ together with the nitrogen to which they are attached form a 3-7 membered cyclic amino group, optionally substituted by one or more substituents selected from: halogen, hydroxyl, cyano, C$_{1-4}$-alkyl, halo-C$_{1-4}$-alkyl, C$_{1-4}$-alkoxy, halo-C$_{1-4}$-alkoxy, —CONH$_2$, —SO$_2$NH$_2$, —NH$_2$, —NHC$_{1-4}$-alkyl, —NHhalo-C$_{1-4}$-alkyl;

X is selected from —N═ or —C($R^2$)═;

$R^2$ is selected from hydrogen, halogen, cyano, $C_{1-4}$-alkyl, halo-$C_{1-4}$-alkyl, cyano-$C_{1-4}$-alkyl, —$OR^5$, —$NR^{4A}R^{4B}$, —$NR^6C(O)OR^5$, —$NR^6C(O)R^5$, —$NR^6C(O)NR^{4A}R^{4B}$, —$C(O)NR^{4A}R^{4B}$, —$C(O)R^5$, —$C(O)OR^5$, —$SO_2R^5$, —$SO_2NR^{4A}R^{4B}$ and —$NR^6S(O)_2R^5$;

W is a phenyl ring or a 5 or 6-membered heteroaryl ring, either ring being optionally substituted with one or more substituents selected from halogen, cyano, oxo $C_{1-4}$-alkyl, halo-$C_{1-4}$-alkyl, cyano-$C_{1-4}$-alkyl, —$OR^5$, —$NR^{7A}R^{7B}$, —$NR^6C(O)OR^5$, —$NR^6C(O)R^5$, —$NR^6C(O)NR^{7A}R^{7B}$, —$C(O)NR^{7A}R^{7B}$, —$C(O)R^5$, —$C(O)OR^5$, —$SO_2R^5$, —$SO_2NR^{7A}R^{7B}$ and —$NR^6S(O)_2R^5$;

$R^{7A}$ and $R^{7B}$ are independently hydrogen, $C_{1-4}$-alkyl or halo-$C_{1-4}$-alkyl.

V is selected from a bond, —O—, —N($R^6$)—, —(C═O)—, —$CONR^6$—, —$NR^6C(O)$—, or —$C_{1-4}$-alkylene-, wherein the $C_{1-4}$-alkylene group is optionally substituted by halogen, and wherein any one of the carbon atoms of the $C_{1-4}$-alkylene group may be replaced by —O— or —N($R^6$)—;

$R^3$ is selected from hydrogen, —$C_{1-4}$-alkyl, —$C_{1-4}$-alkyl-$C_{1-4}$-alkoxy or a 3-7 membered heterocyclic ring or 3-7 membered cycloalkyl ring, or a 5 or 6-membered heteroaryl ring, any one of the rings being optionally substituted with one or more substituents selected from halogen, oxo, hydroxyl, cyano, $C_{1-4}$-alkyl, halo-$C_{1-4}$-alkyl, cyano-$C_{1-4}$-alkyl, —$OR^5$, —$NR^{4A}R^{4B}$, —$NR^6C(O)OR^5$, —$NR^6C(O)R^5$, —$NR^6C(O)NR^{4A}R^{4B}$, —$C(O)NR^{4A}R^{4B}$, —$C(O)R^5$, —$C(O)OR^5$, —$SO_2R^5$, —$SO_2NR^{4A}R^{4B}$ and —$NR^6S(O)_2R^5$;

PROVIDED THAT groups —$WVR^3$ and/or $R^1$ are not:

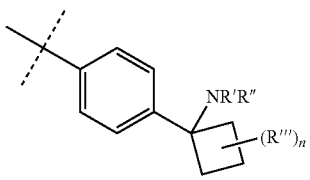

wherein n is 0, 1, or 2;

R' and R" are independently selected from the group consisting of H, —$C_1$-$C_6$alkyl, —(C═O)—$C_1$-$C_6$ alkyl and —(C═O)OC($CH_3$)$_3$; and R''' is H, OH, or $C_1$-$C_6$ alkyl.

Our co-pending International Patent Application No. PCT/GB2014/050765 relates also to SSAO inhibitors of formula (Ia) or a pharmaceutically acceptable salt, or N-oxide thereof:

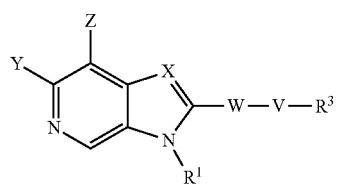
(Ia)

Wherein:

Y is selected from hydrogen, hydroxyl, —$NH_2$, —NH—$C_{1-4}$-alkyl, —NH-halo-$C_{1-4}$-alkyl, or —$C_{1-4}$-alkoxy;

Z is selected from hydrogen, halogen, hydroxyl, cyano, $C_{1-4}$-alkyl, halo-$C_{1-4}$-alkyl, $C_{1-4}$-alkoxy, halo-$C_{1-4}$-alkoxy, —$CONH_2$, —$SO_2NH_2$, —$NH_2$, —$NHC_{1-4}$-alkyl, or —NHhalo-$C_{1-4}$-alkyl;

$R^1$ is a phenyl ring, or a 5 or 6-membered heteroaryl ring, either ring being optionally substituted with one or more substituents selected from halogen, cyano, $C_{1-4}$-alkyl, halo-$C_{1-4}$-alkyl, cyano-$C_{1-4}$-alkyl, —$OR^5$, —$NR^{4A}R^{4B}$, —$NR^6C(O)OR^5$, —$NR^6C(O)R^5$, —$NR^6C(O)NR^{4A}R^{4B}$, —$C(O)NR^{4A}R^{4B}$, —$C(O)R^5$, —$C(O)OR^5$, and —$NR^6S(O)_2R^5$;

wherein $R^{4A}$, $R^{4B}$ $R^5$ and $R^6$ are each independently selected from hydrogen, $C_{1-4}$-alkyl or halo-$C_{1-4}$-alkyl, or $R^{4A}$ and $R^{4B}$ together with the nitrogen to which they are attached form a 3-7 membered cyclic amino group, optionally substituted by one or more substituents selected from: halogen, hydroxyl, cyano, $C_{1-4}$-alkyl, halo-$C_{1-4}$-alkyl, $C_{1-4}$-alkoxy, halo-$C_{1-4}$-alkoxy, —$CONH_2$, —$SO_2NH_2$, —$NH_2$, —$NHC_{1-4}$-alkyl, —NHhalo-$C_{1-4}$-alkyl;

X is selected from —N═ or —C($R^2$)═;

$R^2$ is selected from hydrogen, halogen, cyano, $C_{1-4}$-alkyl, halo-$C_{1-4}$-alkyl, cyano-$C_{1-4}$-alkyl, —$OR^5$, —$NR^{4A}R^{4B}$, —$NR^6C(O)OR^5$, —$NR^6C(O)R^5$, —$NR^6C(O)NR^{4A}R^{4B}$, —$C(O)NR^{4A}R^{4B}$, —$C(O)R^5$, —$C(O)OR^5$, —$SO_2R^5$, —$SO_2NR^{4A}R^{4B}$ and —$NR^6S(O)_2R^5$;

W is a phenyl ring or a 5 or 6-membered heteroaryl ring, either ring being optionally substituted with one or more substituents selected from halogen, cyano, $C_{1-4}$-alkyl, halo-$C_{1-4}$-alkyl, cyano-$C_{1-4}$-alkyl, —$OR^5$, —$NR^{7A}R^{7B}$, —$NR^6C(O)OR^5$, —$NR^6C(O)R^5$, —$NR^6C(O)NR^{7A}R^{7B}$, —$C(O)NR^{7A}R^{7B}$, —$C(O)R^5$, —$C(O)OR^5$, —$SO_2R^5$, —$SO_2NR^{7A}R^{7B}$ and —$NR^6S(O)_2R^5$;

$R^{7A}$ and $R^{7B}$ are independently hydrogen, $C_{1-4}$-alkyl or halo-$C_{1-4}$-alkyl.

V is selected from a bond, —O—, —N($R^6$)—, —(C═O)—, —$CONR^6$—, —$NR^6C(O)$—, or —$C_{1-4}$-alkylene-, wherein the $C_{1-4}$-alkylene group is optionally substituted by halogen, and wherein any one of the carbon atoms of the $C_{1-4}$-alkylene group may be replaced by —O— or —N($R^6$)—;

$R^3$ is hydrogen, or a 3-7 membered heterocyclic ring, or 3-7 membered cycloalkyl ring (optionally selected from cyclopropyl, cyclopentyl or cyclohexyl), or a 5 or 6-membered heteroaryl ring, any one of the rings being optionally substituted with one or more substituents selected from halogen, oxo, hydroxyl, cyano, $C_{1-4}$-alkyl, halo-$C_{1-4}$-alkyl, cyano-$C_{1-4}$-alkyl, —$OR^5$, —$NR^{4A}R^{4B}$, —$NR^6C(O)OR^5$, —$NR^6C(O)R^5$, —$NR^6C(O)NR^{4A}R^{4B}$, —$C(O)NR^{4A}R^{4B}$, —$C(O)R^5$, —$C(O)OR^5$, —$SO_2R^5$, —$SO_2NR^{4A}R^{4B}$ and —$NR^6S(O)_2R^5$. In an embodiment of the compound as defined in formula (Ia), $R^3$ is a 3-7 membered cycloalkyl ring selected from cyclopropyl, cyclopentyl or cyclohexyl.

DETAILED DESCRIPTION OF THE INVENTION

It has surprisingly been found that the compounds of formula (I) below are inhibitors of SSAO. They are therefore useful for the treatment or prevention of diseases in which inhibition of SSAO activity is beneficial, such as inflammation, inflammatory diseases, immune or autoimmune disorders, and inhibition of tumour growth.

The present invention makes available a compound of formula (I) or a pharmaceutically acceptable salt, or N-oxide thereof:

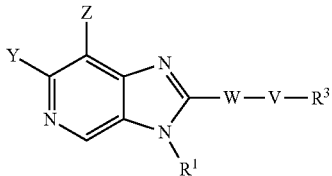

(I)

Wherein:

Y is selected from hydrogen, hydroxyl, —NH$_2$, —NH—C$_{1-4}$-alkyl, —NH-halo-C$_{1-4}$-alkyl, or —C$_{1-4}$-alkoxy;

Z is selected from hydrogen, halogen, hydroxyl, cyano, C$_{1-4}$-alkyl, halo-C$_{1-4}$-alkyl, C$_{1-4}$-alkoxy, halo-C$_{1-4}$-alkoxy, —CONH$_2$, —SO$_2$NH$_2$, —NH$_2$, —NHC$_{1-4}$-alkyl, or —NHhalo-C$_{1-4}$-alkyl;

R$^1$ is a phenyl ring, or a 5 or 6-membered heteroaryl ring, either ring optionally substituted with one or more substituents selected from halogen, cyano, C$_{1-4}$-alkyl, halo-C$_{1-4}$-alkyl, cyano-C$_{1-4}$-alkyl, —OR$^5$, —NR$^{4A}$R$^{4B}$, —NR$^6$C(O)OR$^5$, —NR$^6$C(O)R$^5$, —NR$^6$C(O)NR$^{4A}$R$^{4B}$, —C(O)NR$^{4A}$R$^{4B}$, —C(O)R$^5$, —C(O)OR$^5$, and —NR$^6$S(O)$_2$R$^5$; wherein R$^{4A}$, R$^{4B}$ R$^5$ and R$^6$ are each independently selected from hydrogen, C$_{1-4}$-alkyl or halo-C$_{1-4}$-alkyl, or R$^{4A}$ and R$^{4B}$ together with the nitrogen to which they are attached form a 3-7 membered cyclic amino group, optionally substituted by one or more substituents selected from: halogen, hydroxyl, cyano, C$_{1-4}$-alkyl, halo-C$_{1-4}$-alkyl, C$_{1-4}$-alkoxy, halo-C$_{1-4}$-alkoxy, —CONH$_2$, —SO$_2$NH$_2$, —NH$_2$, —NHC$_{1-4}$-alkyl, —NHhalo-C$_{1-4}$-alkyl;

R$^{7A}$ and R$^{7B}$ are independently hydrogen, C$_{1-4}$-alkyl or halo-C$_{1-4}$-alkyl; and wherein the group —WVR$^3$ is selected from any one of groups (i)-(iv):

(i) W is a [6,5], [5,6], or [6,6] heteroaryl ring system comprising a phenyl ring or a 6-membered heteroaryl ring fused to a 5 or 6-membered heteroaryl or heterocyclic ring, the fused ring system being optionally substituted on either or both rings with one or more groups selected from halogen, oxo, hydroxyl, cyano, C$_{1-4}$-alkyl, halo-C$_{1-4}$-alkyl, cyano-C$_{1-4}$-alkyl, —OR$^5$, —NR$^{4A}$R$^{4B}$, —NR$^6$C(O)OR$^5$, —NR$^6$C(O)R$^5$, —NR$^6$C(O)NR$^{4A}$R$^{4B}$, —C(O)NR$^{4A}$R$^{4B}$, —C(O)R$^5$, —C(O)OR$^5$, —SO$_2$R$^5$, —SO$_2$NR$^{4A}$R$^{4B}$ and —NR$^6$S(O)$_2$R$^5$, and V is a direct bond, and R$^3$ is hydrogen;

(ii) W is a phenyl ring or a 5 or 6-membered heteroaryl ring, either ring optionally substituted with one or more groups selected from halogen, oxo, hydroxyl, cyano, C$_{1-4}$-alkyl, halo-C$_{1-4}$-alkyl, cyano-C$_{1-4}$-alkyl, —OR$^5$, —NR$^{4A}$R$^{4B}$, —NR$^6$C(O)OR$^5$, —NR$^6$C(O)R$^5$, —NR$^6$C(O)NR$^{4A}$R$^{4B}$, —C(O)NR$^{4A}$R$^{4B}$, —C(O)R$^5$, —C(O)OR$^5$, —SO$_2$R$^5$, —SO$_2$NR$^{4A}$R$^{4B}$ and —NR$^6$S(O)$_2$R$^5$, and V is —NR$^6$—, and R$^3$ is a C$_{1-6}$-alkyl group substituted with one or more substituents selected from the group consisting of: halogen, hydroxyl, cyano, oxo, and NR$^{7A}$R$^{7B}$;

(iii) W is a 5 or 6-membered heterocyclic ring optionally substituted with one or more substituents selected from halogen, oxo, hydroxyl, cyano, C$_{1-4}$-alkyl, halo-C$_{1-4}$-alkyl, cyano-C$_{1-4}$-alkyl, —OR$^5$, —NR$^{4A}$R$^{4B}$, —NR$^6$C(O)OR$^5$, —NR$^6$C(O)R$^5$, —NR$^6$C(O)NR$^{4A}$R$^{4B}$, —C(O)NR$^{4A}$R$^{4B}$, —C(O)R$^5$, —C(O)OR$^5$, —SO$_2$R$^5$, —SO$_2$NR$^{4A}$R$^{4B}$ and —NR$^6$S(O)$_2$R$^5$, V is a direct bond, and R$^3$ is a phenyl ring or a 5 or 6-membered heteroaryl ring optionally substituted with one or more substituents selected from halogen, oxo, hydroxyl, cyano, C$_{1-4}$-alkyl, halo-C$_{1-4}$-alkyl, cyano-C$_{1-4}$-alkyl, —OR$^5$, —NR$^{4A}$R$^{4B}$, —NR$^6$C(O)OR$^5$, —NR$^6$C(O)R$^5$, —NR$^6$C(O)NR$^{4A}$R$^{4B}$, —C(O)NR$^{4A}$R$^{4B}$, —C(O)R$^5$, —C(O)OR$^5$, —SO$_2$R$^5$, —SO$_2$NR$^{4A}$R$^{4B}$ and —NR$^6$S(O)$_2$R$^5$;

(iv) W is a direct bond, V is a group selected from —(C═O)—(CH$_2$)$_n$—, —CONR$^6$—(CH$_2$)$_n$—, —NR$^6$C(O)—(CH$_2$)$_n$—, —NR$^6$C(O)O—(CH$_2$)$_n$—, or —C$_{1-4}$-alkylene-, wherein the C$_{1-4}$-alkylene group and/or the (CH$_2$)$_n$ group is optionally substituted by halogen, and wherein any one of the carbon atoms of the C$_{1-4}$-alkylene group may be replaced by —O— or —N(R$^6$)—, and n is 0, 1, 2, 3, or 4

R$^3$ is selected from a C$_{1-6}$-alkyl group optionally substituted with one or more substituents selected from the group consisting of: halogen, hydroxyl, cyano, oxo, C1-4 alkoxy, C1-4alkoxy and NR$^{7A}$R$^{7B}$; or a 3-7 membered heterocyclic or cycloalkyl ring, a phenyl ring, or a 5 or 6-membered heteroaryl ring, any of which rings is optionally substituted with a group selected from halogen, oxo, hydroxyl, cyano, C$_{1-4}$-alkyl, halo-C$_{1-4}$-alkyl, cyano-C$_{1-4}$-alkyl, —OR$^5$, —NR$^{4A}$R$^{4B}$, —NR$^6$C(O)OR$^5$, —NR$^6$C(O)R$^5$, —NR$^6$C(O)NR$^{4A}$R$^{4B}$, —C(O)NR$^{4A}$R$^{4B}$, —C(O)R$^5$, —C(O)OR$^5$, —SO$_2$R$^5$, —SO$_2$NR$^{4A}$R$^{4B}$ and —NR$^6$S(O)$_2$R$^5$.

Definitions

The following definitions shall apply throughout the specification and the appended claims, unless otherwise stated or indicated.

The term "C$_{1-6}$-alkyl" denotes a straight or branched alkyl group having from 1 to 6 carbon atoms. For parts of the range C$_{1-6}$-alkyl all subgroups thereof are contemplated such as C$_{1-5}$-alkyl, C$_{1-4}$-alkyl, C$_{2-4}$-alkyl, C$_{2-3}$-alkyl and C$_{3-4}$-alkyl. Examples of said C$_{1-6}$-alkyl include methyl, ethyl, n-propyl, isopropyl, n-butyl, isobutyl, sec-butyl and tert-butyl, n-pentyl, and n-hexyl.

Unless otherwise specified, the term "C$_{3-7}$-cycloalkyl" refers to a monocyclic saturated or partially unsaturated hydrocarbon ring system having from 3 to 7 carbon atoms. Examples of said C$_{3-7}$-cycloalkyl include cyclopropyl, cyclobutyl, cyclopentyl, cyclohexyl, cyclohexenyl, cycloheptyl, and cycloheptenyl. For parts of the range "C$_{3-7}$-cycloalkyl" all subgroups thereof are contemplated such as C$_{3-7}$-cycloalkyl, C$_{3-6}$-cycloalkyl, C$_{3-5}$-cycloalkyl, C$_{3-4}$-cycloalkyl, C$_{4-7}$-cycloalkyl, C$_{4-6}$-cycloalkyl, C$_{4-5}$-cycloalkyl, C$_{5-7}$-cycloalkyl, C$_{5-6}$-cycloalkyl, and C$_{6-7}$-cycloalkyl.

The term "C$_{1-4}$-alkoxy" refers to a straight or branched C$_{1-4}$-alkyl group which is attached to the remainder of the molecule through an oxygen atom. For parts of the range C$_{1-4}$-alkoxy, all subgroups thereof are contemplated such as C$_{1-3}$-alkoxy, C$_{1-2}$-alkoxy, C$_{2-4}$-alkoxy, C$_{2-3}$-alkoxy and C$_{3-4}$-alkoxy. Examples of said C$_{1-4}$-alkoxy include methoxy, ethoxy, n-propoxy, isopropoxy, n-butoxy, isobutoxy, sec-butoxy and tert-butoxy.

The term "haloC$_{1-4}$-alkoxy" refers to a straight or branched C$_{1-4}$-alkyl group which is attached to the remainder of the molecule through an oxygen atom and has one or more hydrogen atoms thereof replaced with halogen such as fluoro or chloro. For parts of the range C$_{1-4}$-alkoxy, all subgroups thereof are contemplated. Examples of said $C_{1-4}$-alkoxy include trifluoromethoxy.

The term "hydroxy-$C_{1-4}$-alkyl" denotes a straight or branched $C_{1-4}$-alkyl group that has one or more hydrogen atoms thereof replaced with OH. Examples of said hydroxy-$C_{1-4}$-alkyl include hydroxymethyl, 2-hydroxyethyl and 2,3-dihydroxypropyl.

The term "halo-$C_{1-4}$-alkyl" denotes a straight or branched $C_{1-4}$-alkyl group that has one or more hydrogen atoms thereof replaced with halogen. Examples of said halo-$C_{1-4}$-alkyl include fluoromethyl, trifluoromethyl, trichloromethyl and 2-fluoroethyl.

The term "cyano-$C_{1-4}$-alkyl" denotes a straight or branched $C_{1-4}$-alkyl group that has one or more hydrogen atoms thereof replaced with cyano. Examples of said cyano-$C_{1-4}$-alkyl include cyanomethyl, 2-cyanoethyl and 3-cyanopropyl.

The terms "heteroaryl" and "heteroaromatic ring" denote a monocyclic heteroaromatic ring comprising 5 to 6 ring atoms in which one or more of the ring atoms are other than carbon, such as nitrogen, sulphur or oxygen. Examples of heteroaryl groups include furyl, pyrrolyl, thienyl, oxazolyl, isoxazolyl, imidazolyl, thiazolyl, isothiazolyl, pyridinyl, pyrimidinyl, tetrazolyl, pyrazolyl, pyridazinyl, pyrazinyl and thiadiazolyl.

The terms "heterocyclyl" and "heterocyclic ring" denote a non-aromatic, fully saturated or partially unsaturated, preferably fully saturated, monocyclic ring system having from 3 to 7 ring atoms, especially 5 or 6 ring atoms, in which one or more of the ring atoms are other than carbon, such as nitrogen, sulphur or oxygen. Examples of heterocyclic groups include piperidinyl, morpholinyl, homomorpholinyl, azepanyl, piperazinyl, oxo-piperazinyl, diazepinyl, tertahydropyridinyl, tetrahydropyranyl, pyrrolidinyl, tertrahydrofuranyl, and dihydropyrrolyl, groups.

The term "heterocyclic-$C_{1-4}$-alkyl" refers to a heterocyclic ring that is directly linked to a straight or branched $C_{1-4}$-alkyl group via a carbon or nitrogen atom of said ring. Examples of said heterocyclic-$C_{1-4}$-alkyl include piperidin-4-ylmethyl, piperidin-1-ylmethyl, morpholin-4-yl-methyl and piperazin-4-ylmethyl. The $C_{1-4}$-alkyl part, which includes methylene, ethylene, propylene or butylene, is optionally substituted by one or more substituents selected from halogen, amino, methoxy, or hydroxyl.

The term "$C_{1-4}$-alkylene" denotes a straight or branched divalent saturated hydrocarbon chain having from 1 to 4 carbon atoms. The $C_{1-4}$-alkylene chain may be attached to the rest of the molecule and to the radical group through one carbon within the chain or through any two carbons within the chain. Examples of $C_{1-4}$-alkylene radicals include methylene [—$CH_2$—], 1,2-ethylene [—$CH_2$—$CH_2$—], 1,1-ethylene [—$CH(CH_3)$—], 1,2-propylene [—$CH_2$—CH($CH_3$)—] and 1,3-propylene [—$CH_2$—$CH_2$—$CH_2$—]. When referring to a "$C_{1-4}$-alkylene" radical, all subgroups thereof are contemplated, such as $C_{1-2}$-alkylene, $C_{2-3}$-alkylene, or $C_{3-4}$-alkylene.

"Halogen" refers to fluorine, chlorine, bromine or iodine, preferably fluorine and chlorine, most preferably fluorine.

"Hydroxy" refers to the —OH radical.

"Cyano" refers to the —CN radical.

"Oxo" refers to the carbonyl group =O.

"Optional" or "optionally" means that the subsequently described event or circumstance may but need not occur, and that the description includes instances where the event or circumstance occurs and instances in which it does not.

"Pharmaceutically acceptable" means being useful in preparing a pharmaceutical composition that is generally safe, non-toxic and neither biologically nor otherwise undesirable and includes being useful for veterinary use as well as human pharmaceutical use.

"Treatment" as used herein includes prophylaxis of the named disorder or condition, or amelioration or elimination of the disorder once it has been established.

"An effective amount" refers to an amount of a compound that confers a therapeutic effect on the treated subject. The therapeutic effect may be objective (i.e., measurable by some test or marker) or subjective (i.e., subject gives an indication of or feels an effect).

"Prodrugs" refers to compounds that may be converted under physiological conditions or by solvolysis to a biologically active compound of the invention. A prodrug may be inactive when administered to a subject in need thereof, but is converted in vivo to an active compound of the invention. Prodrugs are typically rapidly transformed in vivo to yield the parent compound of the invention, e.g. by hydrolysis in the blood. The prodrug compound usually offers advantages of solubility, tissue compatibility or delayed release in a mammalian organism (see Silverman, R. B., *The Organic Chemistry of Drug Design and Drug Action*, $2^{nd}$ Ed., Elsevier Academic Press (2004), pp. 498-549). Prodrugs of a compound of the invention may be prepared by modifying functional groups, such as a hydroxy, amino or mercapto groups, present in a compound of the invention in such a way that the modifications are cleaved, either in routine manipulation or in vivo, to the parent compound of the invention. Examples of prodrugs include, but are not limited to, acetate, formate and succinate derivatives of hydroxy functional groups or phenyl carbamate derivatives of amino functional groups.

Throughout the specification and the appended claims, a given chemical formula or name shall also encompass all salts, hydrates, solvates, N-oxides and prodrug forms thereof. Further, a given chemical formula or name shall encompass all tautomeric and stereoisomeric forms thereof. Tautomers include enol and keto forms. Stereoisomers include enantiomers and diastereomers. Enantiomers can be present in their pure forms, or as racemic (equal) or unequal mixtures of two enantiomers. Diastereomers can be present in their pure forms, or as mixtures of diastereomers. Diastereomers also include geometrical isomers, which can be present in their pure cis or trans forms or as mixtures of those.

The compounds of formula (I) may be used as such or, where appropriate, as pharmacologically acceptable salts (acid or base addition salts) thereof. The pharmacologically acceptable addition salts mentioned below are meant to comprise the therapeutically active non-toxic acid and base addition salt forms that the compounds are able to form. Compounds that have basic properties can be converted to their pharmaceutically acceptable acid addition salts by treating the base form with an appropriate acid. Exemplary acids include inorganic acids, such as hydrogen chloride, hydrogen bromide, hydrogen iodide, sulphuric acid, phosphoric acid; and organic acids such as formic acid, acetic acid, propanoic acid, hydroxyacetic acid, lactic acid, pyruvic acid, glycolic acid, maleic acid, malonic acid, oxalic acid, benzenesulphonic acid, toluenesulphonic acid, methanesulphonic acid, trifluoroacetic acid, fumaric acid, succinic acid, malic acid, tartaric acid, citric acid, salicylic acid, p-aminosalicylic acid, pamoic acid, benzoic acid, ascorbic acid and the like. Exemplary base addition salt forms are the sodium, potassium, calcium salts, and salts with pharmaceutically acceptable amines such as, for example, ammonia, alkylamines, benzathine, and amino acids, such as, e.g. arginine and lysine. The term addition salt as used herein also comprises solvates which the compounds and salts thereof are able to form, such as, for example, hydrates, alcoholates and the like.

The Group Y

In an embodiment Y selected is from hydrogen, hydroxyl, —$NH_2$, —NH—$C_{1-4}$-alkyl such as —NH-Methyl, —NH-ethyl, or —NH-isopropyl, —NH-halo-$C_{1-4}$-alkyl such as— NHtrifluoromethyl, or —$C_{1-4}$-alkoxy such as methoxy. In an embodiment Y is hydrogen.

The Group Z

In an embodiment Z is hydrogen, halogen such as fluoro or chloro, hydroxyl, cyano, $C_{1-4}$-alkyl such as methyl or isopropyl, halo-$C_{1-4}$-alkyl such as triflouromethyl, $C_{1-4}$-alkoxy such as methoxy, halo-$C_{1-4}$-alkoxy such as trifluoromethoxy, —$CONH_2$, —$SO_2NH_2$, —$NH_2$, —$NHC_{1-4}$-alkyl such as —NH-Methyl, —NH-ethyl, or —NH-isopropyl, or —NHhalo-$C_{1-4}$-alkyl. In an embodiment Z is hydrogen.

The Group $R^1$

In an embodiment $R^1$ is a phenyl ring, or a 5 or 6-membered heteroaryl ring either ring being optionally substituted with one or more substituents selected from halogen such as fluoro or chloro, cyano, $C_{1-4}$-alkyl such as methyl or isopropyl, halo-$C_{1-4}$-alkyl such as trifluoromethyl, cyano-$C_{1-4}$-alkyl such as methylcyano, —$OR^5$ such as methoxy or trifluoromethoxy, —$NR^{4A}R^{4B}$ such as —$NH_2$, —NHMethyl, —NHisopropyl, —$NR^6C(O)OR^5$, —$NR^6C(O)R^5$, —$NR^6C(O)NR^{4A}R^{4B}$, —$C(O)NR^{4A}R^{4B}$, —$C(O)R^5$ such as —$COCH_3$, —$C(O)OR^5$, and —$NR^6S(O)_2R^5$. In an embodiment $R^1$ is optionally substituted phenyl, pyridyl, pyrrole, furan, imidazole, or thiophene. In an embodiment $R^1$ is optionally substituted with one or more substituents selected from halogen and $C_{1-4}$alkyl, preferably the halogen is fluoro or chloro, and the $C_{1-4}$alkyl group is methyl.

In an embodiment $R^1$ is a phenyl ring, or a 5 or 6-membered heteroaryl ring substituted with a 3-7 membered cycloalkyl group such as cyclopropyl, cyclobutyl, cyclopentyl, cyclohexyl; preferably cyclopropyl.

$R^{4A}$, $R^{4B}$ $R^5$ and $R^6$ are each independently selected from hydrogen, $C_{1-4}$-alkyl such as methyl, ethyl or isopropyl, or halo-$C_{1-4}$-alkyl such as trifluoromethyl, or $R^{4A}$ and $R^{4B}$ together with the nitrogen to which they are attached form a 3-7 membered cyclic amino group such as aziridine, azetidine, oxetane, pyrrolidine, piperidine, piperazine, homopiperidine, homopiperazine, morpholine, or tetrahydrofuran, optionally substituted by one or more substituents selected from: halogen such as fluoro or chloro, hydroxyl, cyano, $C_{1-4}$-alkyl such as methyl or isopropyl, halo-$C_{1-4}$-alkyl such as trifluoromethyl, $C_{1-4}$-alkoxy such as methoxy, halo-$C_{1-4}$-alkoxy such as trifluoromethoxy, —$CONH_2$, —$SO_2NH_2$, —$NH_2$, —$NHC_{1-4}$-alkyl, —NHhalo-$C_{1-4}$-alkyl;

$R^{7A}$ and $R^{7B}$ are independently hydrogen, $C_{1-4}$-alkyl such as methyl or isopropyl, or halo-$C_{1-4}$-alkyl such as trifluoromethyl.

The group —$WVR^3$ is selected from any one of embodiments (i)-(iv), referred to as the first, second, third and fourth embodiments respectively:

(i) In a first embodiment, W is a [6,5], [5,6], or [6,6] heteroaryl ring system comprising a phenyl ring or a 6-membered heteroaryl ring such as pyridinyl, pyridazinyl, pyrazinyl, or pyrimidinyl fused to a 5 or 6-membered heteroaryl such as pyridinyl, pyridazinyl, pyrazinyl, pyrimidinyl, imidazolyy, oxazolyl, or thiazolyl or a heterocyclic ring such as pyrrolidinyl, the fused ring system being optionally substituted on either or both rings with one or more groups selected from halogen such as chloro and fluoro, oxo, hydroxyl, cyano, $C_{1-4}$-alkyl such as methyl, ethyl and isopropyl, halo-$C_{1-4}$-alkyl such as trifluoromethyl, cyano-$C_{1-4}$-alkyl such as cyanomethyl, —$OR^5$ such as methoxy, —$NR^{4A}R^{4B}$ such as —$NH_2$, NHMe, or —$N(Me)_2$, —$NR^6C(O)OR^5$, —$NR^6C(O)R^5$, —$NR^6C(O)NR^{4A}R^{4B}$, —$C(O)NR^{4A}R^{4B}$, —$C(O)R^5$, —$C(O)OR^5$, —$SO_2R^5$, —$SO_2NR^{4A}R^{4B}$ and —$NR^6S(O)_2R^5$, and V is a direct bond, and $R^3$ is hydrogen.

In an embodiment W is a [6,5] heteroaryl ring system, wherein the 6 membered ring is phenyl, and the 5-membered ring is pyrrolidinyl or imidazolyl and wherein the [6,5] ring system is connected to the rest of the molecule (i.e. the imidazopyridine core bearing Y, Z, and $R^1$) via the phenyl ring, and wherein either ring is optionally substituted as set out in claim 1. Preferred optional substituents on the W ring system are halogen, oxo and $C_{1-4}$-alkyl.

In an embodiment the group —$WVR^3$ is A1 or A2 wherein the —$WVR^3$ group is connected to the rest of the molecule via a phenyl ring carbon atom.

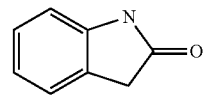

(A1)

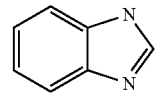

(A2)

(ii) In a second embodiment W is a phenyl ring or a 5 or 6-membered heteroaryl ring such as pyridinyl, pyridazinyl, pyrazinyl, pyrimidinyl, imidazolyl, oxazolyl, or thiazolyl, either ring optionally substituted with one or more groups selected from halogen such as fluoro or chloro, oxo, hydroxyl, cyano, $C_{1-4}$-alkyl such as methyl, ethyl and isopropyl, halo-$C_{1-4}$-alkyl such as trifluoromethyl, cyano-$C_{1-4}$-alkyl such as cyanomethyl, —$OR^5$ such as methoxy, —$NR^{4A}R^{4B}$, —$NR^6C(O)OR^5$, —$NR^6C(O)R^5$, —$NR^6C(O)NR^{4A}R^{4B}$, —$C(O)NR^{4A}R^{4B}$, —$C(O)R^5$, —$C(O)OR^5$, —$SO_2R^5$, —$SO_2NR^{4A}R^{4B}$ and —$NR^6S(O)_2R^5$, and V is —$NR^6$— such as —NH—, or —$N(CH_3)$—, and $R^3$ is a $C_{1-6}$-alkyl group such as methyl, ethyl, propyl, isopropyl, n-butyl, isobutyl, sec-butyl, or tert-butyl substituted with one or more substituents selected from the group consisting of: halogen, hydroxyl, cyano, oxo, and $NR^{7A}R^{7B}$ such as —$NH_2$, —$NHCH_3$, —$N(CH_3)_2$. Preferably $R^3$ is substituted with one or more substituents selected from: hydroxyl, fluoro, chloro, and cyano.

In an embodiment W is a phenyl or 6 membered heteroaryl ring substituted in a 1,4 (i.e. para) pattern—in other words so that the atom to which the —$VR^3$ group is connected is separated by two ring atoms from the atom to which the rest of the molecule is connected. In an embodiment, W is a ring selected from phenyl, pyridinyl or pyrimidinyl. In an embodiment V is —NH— or —$N(CH_3)$—. In an embodiment $R^3$ is —$(CH_2)C(CH_3)_2OH$.

In an embodiment W is a divalent group selected from any one of the following rings, any of which rings is optionally substituted as set out in claim 1

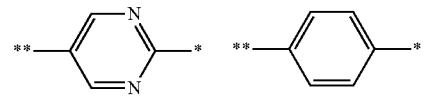

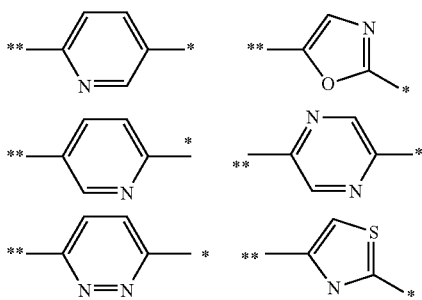

wherein the bond marked ** is directly connected to the rest of the molecule and the atom marked * is directly connected to V.

(iii) In the third embodiment W is a 5 or 6-membered heterocyclic ring such as piperidinyl, morpholinyl, or pyrrolidinyl optionally substituted with one or more substituents selected from halogen such as fluoro or chloro, oxo, hydroxyl, cyano, $C_{1-4}$-alkyl such as methyl, ethyl and isopropyl, halo-$C_{1-4}$-alkyl such as trifluoromethyl, cyano-$C_{1-4}$-alkyl such as cyanomethyl, —$OR^5$ such as methoxy, —$NR^{4A}R^{4B}$, —$NR^6C(O)OR^5$, —$NR^6C(O)R^5$, —$NR^6C(O)NR^{4A}R^{4B}$, —$C(O)NR^{4A}R^{4B}$, —$C(O)R^5$, —$C(O)OR^5$, —$SO_2R^5$, —$SO_2NR^{4A}R^{4B}$ and —$NR^6S(O)_2R^5$, V is a direct bond, and $R^3$ is a phenyl ring or a 5 or 6-membered heteroaryl ring such as pyridinyl, pyridazinyl, pyrazinyl, pyrimidinyl, imidazolyl, oxazolyl, or thiazolyl optionally substituted with one or more substituents selected from halogen such as fluoro or chloro, oxo, hydroxyl, cyano, $C_{1-4}$-alkyl such as methyl, ethyl and isopropyl, halo-$C_{1-4}$-alkyl such as trifluoromethyl, cyano-$C_{1-4}$-alkyl such as cyanomethyl, —$OR^5$ such as methoxy, —$NR^{4A}R^{4B}$, —$NR^6C(O)OR^5$, —$NR^6C(O)R^5$, —$NR^6C(O)NR^{4A}R^{4B}$, —$C(O)NR^{4A}R^{4B}$, —$C(O)R^5$, —$C(O)OR^5$, —$SO_2R^5$, —$SO_2NR^{4A}R^{4B}$ and —$NR^6S(O)_2R^5$. In an embodiment W is a 6 membered heteroaryl ring substituted in a 1,4 pattern—in other words so that the atom to which the —$R^3$ group is connected is separated by two ring atoms from the atom to which the rest of the molecule is connected. In an embodiment W is a piperidine ring.

In an embodiment the group —$WVR^3$ is:

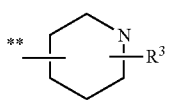

wherein the bond marked ** is directly connected to the rest of the molecule.

In an embodiment the group —$WVR^3$ is:

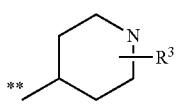

In an embodiment the group —$WVR^3$ is:

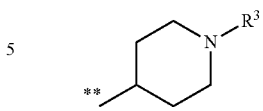

In an embodiment $R^3$ is selected from phenyl, pyridyl and pyrimidinyl, any of which is optionally substituted with one or more groups selected from fluoro, chloro, oxo and $C_{1-4}$-alkyl. In an embodiment $R^3$ is selected from phenyl, pyridyl and pyrimidinyl, any of which is optionally substituted with oxo.

(iv) In the fourth embodiment W is a direct bond, V is a group selected from —(C═O)—$(CH_2)_n$— such as —C(O)—, —$C(O)CH_2$— or —$C(O)(CH_2)_2$—, -$CONR^6$—$(CH_2)_n$— such as —$C(O)NR^6$—, —$C(O)NR^6CH_2$— or —$C(O)NR^6$—$(CH_2)_2$—, —$NR^6C(O)$($CH_2)_n$— such as —$NR^6C(O)$—, —$NR^6C(O)CH_2$— or —$NR^6C(O)(CH_2)_2$—, or —$NR^6C(O)O$—$(CH_2)_n$— such as —$NR^6C(O)O$—, —$NR^6C(O)OCH_2$— or —$NR^6C(O)O(CH_2)_2$— wherein the bond marked ** is connected to the rest of the molecule, or a $C_{1-4}$ alkylene group (i.e. —$(CH_2)_{1-4}$—) such as —$(CH_2)$—, —$(CH_2)_2$—, —$(CH_2)_3$—, or —$(CH_2)_4$— wherein one or more of the hydrogen atoms on any one of the aforementioned —$(CH_2)$— groups is optionally replaced by halogen such as fluoro, and wherein any one of the carbon atoms of the $C_{1-4}$ alkylene group may be replaced by —O— or —$N(R^6)$—, and n is 0, 1, 2, 3, or 4

$R^3$ is selected from a $C_{1-6}$-alkyl group optionally substituted with one or more substituents selected from the group consisting of: halogen, hydroxyl, cyano, oxo, $C_{1-4}$ alkoxy, $C_{1-4}$haloalkoxy and $NR^{7A}R^{7B}$; or a 3-7 membered heterocyclic or cycloalkyl ring such as such as piperidinyl, pyrrolidinyl, morpholinyl, tetrahydropyranyl, cyclohexyl, cyclopentyl, or cyclopropyl, a phenyl ring, or a 5 or 6-membered heteroaryl ring such as pyridyl, pyridazinyl, pyrazinyl, pyrimidinyl, imidazolyl, oxazolyl, or thiazolyl, any of which rings is optionally substituted with a group selected from halogen such as fluoro or chloro, oxo, hydroxyl, cyano, $C_{1-4}$-alkyl such as methyl, ethyl and isopropyl, halo-$C_{1-4}$-alkyl such as trifluoromethyl, cyano-$C_{1-4}$-alkyl such as cyanomethyl, —$OR^5$ such as methoxy, —$NR^{4A}R^{4B}$, —$NR^6C(O)OR^5$, —$NR^6C(O)R^5$, —$NR^6C(O)NR^{4A}R^{4B}$, —$C(O)NR^{4A}R^{4B}$, —$C(O)R^5$, —$C(O)OR^5$, —$SO_2R^5$, —$SO_2NR^{4A}R^{4B}$ and —$NR^6S(O)_2R^5$.

In an embodiment V is $C_{1-4}$ alkylene group optionally substituted with one or more fluoro, and $R^3$ is phenyl, pyridyl or imidazolyl, any of which rings is optionally substituted as set out in claim 1.

In an embodiment V is —(C═O)—$(CH_2)_n$— or —$CONR^6$—$(CH_2)_n$— and $R^3$ is a 3-7 membered heterocyclic ring optionally substituted as set out in claim 1. In an embodiment $R^3$ is tetrahydropyran.

In one aspect, the invention relates to a compound of formula (I) for use in therapy. The compounds as defined above are useful as inhibitors of SSAO activity. As such, they are useful in the treatment or prevention of conditions and diseases in which inhibition of SSAO activity is beneficial. More specifically, they are useful for the treatment or prevention of inflammation, inflammatory diseases, immune or autoimmune disorders, cystic fibrosis, or inhibition of tumour growth; and they are useful in the manufacture of a medicament for treatment or prevention of inflammation, inflammatory diseases, immune or autoimmune disorders, cystic fibrosis, or inhibition of tumour growth In particular, it is believed that compounds of formula (I) are useful for the treatment or prevention of arthritis (including rheumatoid arthritis, juvenile rheumatoid arthritis, osteoarthritis and psoriatic arthritis), synovitis, vasculitis, Sjogren's disease, a condition associated with inflammation of the bowel (including Crohn's disease, ulcerative colitis, inflammatory bowel disease and irritable bowel syndrome), atherosclerosis, multiple sclerosis, Alzheimer's disease, vascular dementia, Parkinson's disease, cerebral amyloid angiopathy, cerebral autosomal dominant arteriopathy with subcortical infarcts and leukoencephalopathy, a pulmonary inflammatory disease (including asthma, chronic obstructive pulmonary disease and acute respiratory distress syndrome), a fibrotic disease (including idiopathic pulmonary fibrosis, cardiac fibrosis, liver fibrosis and systemic sclerosis (scleroderma)), an inflammatory disease of the skin (including contact dermatitis, atopic dermatitis and psoriasis), an inflammatory disease of the eye (including age related macular degeneration, uveitis and diabetic retinopathy), systemic inflammatory response syndrome, sepsis, an inflammatory and/or autoimmune condition of the liver (including autoimmune hepatitis, primary biliary cirrhosis, alcoholic liver disease, sclerosing cholangitis, and autoimmune cholangitis), diabetes (type I or II) and/or the complications thereof, chronic heart failure, congestive heart failure, an ischemic disease (including stroke and ischemia-reperfusion injury) or myocardial infarction and/or the complications thereof, or epilepsy.

It is believed that the compounds of the invention are especially useful for the treatment or prevention of a disease selected from rheumatoid arthritis, osteoarthritis, liver fibrosis, chronic obstructive pulmonary disease, multiple sclerosis, Sjogren's disease, Alzheimer's disease, Parkinson's disease, inflammatory bowel disease, or vascular dementia.

In view of the evidence cited in the above introduction that VAP-1 is up regulated in several cancers, including gastric cancer, melanoma, hepatoma and head and neck tumours and that mice bearing enzymatically inactive VAP-1 grow melanomas more slowly, and in view of the link between VAP-1 and angiogenesis, it is also expected that the compounds of the invention are anti-angiogenic and therefore have utility in the treatment of cancers by inhibition of tumour growth.

The invention thus includes the compounds of formula (I) above for use in the treatment or prevention of the above-mentioned conditions and diseases. The invention also includes the use of said compounds in the manufacture of a medicament for the treatment or prevention of the above-mentioned conditions and diseases. The invention furthermore includes methods for treatment or prevention of such conditions and diseases, comprising administering to a mammal, including man, in need of such treatment an effective amount of a compound as defined above.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

In other aspects, the methods herein include those further comprising monitoring subject response to the treatment administrations. Such monitoring may include periodic sampling of subject tissue, fluids, specimens, cells, proteins, chemical markers, genetic materials, etc. as markers or indicators of the treatment regimen. In other methods, the subject is prescreened or identified as in need of such treatment by assessment for a relevant marker or indicator of suitability for such treatment.

In one embodiment, the invention provides a method of monitoring treatment progress. The method includes the step of determining a level of diagnostic marker (Marker) (e.g., any target or cell type delineated herein modulated by a compound herein) or diagnostic measurement (e.g., screen, assay) in a subject suffering from or susceptible to a disorder or symptoms thereof delineated herein, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

In certain method embodiments, a level of Marker or Marker activity in a subject is determined at least once. Comparison of Marker levels, e.g., to another measurement of Marker level obtained previously or subsequently from the same patient, another patient, or a normal subject, may be useful in determining whether therapy according to the invention is having the desired effect, and thereby permitting adjustment of dosage levels as appropriate. Determination of Marker levels may be performed using any suitable sampling/expression assay method known in the art or described herein. Preferably, a tissue or fluid sample is first removed from a subject. Examples of suitable samples include blood, urine, tissue, mouth or cheek cells, and hair samples containing roots. Other suitable samples would be known to the person skilled in the art. Determination of protein levels and/or mRNA levels (e.g., Marker levels) in the sample can be performed using any suitable technique known in the art, including, but not limited to, enzyme immunoassay, ELISA, radiolabeling/assay techniques, blotting/chemiluminescence methods, real-time PCR, and the like.

Compositions

A currently preferred embodiment of the invention is a pharmaceutical composition comprising a compound of formula (I), together with one or more pharmaceutically acceptable carriers and/or excipients.

For clinical use, the compounds of the invention are formulated into pharmaceutical formulations for various modes of administration. It will be appreciated that compounds of the invention may be administered together with a physiologically acceptable carrier, excipient, or diluent. The pharmaceutical compositions of the invention may be administered by any suitable route, preferably by oral, rectal, nasal, topical (including buccal and sublingual), sublingual, transdermal, intrathecal, transmucosal or parenteral (including subcutaneous, intramuscular, intravenous and intradermal) administration.

Other formulations may conveniently be presented in unit dosage form, e.g., tablets and sustained release capsules, and in liposomes, and may be prepared by any methods well known in the art of pharmacy. Pharmaceutical formulations are usually prepared by mixing the active substance, or a pharmaceutically acceptable salt thereof, with conventional pharmaceutically acceptable carriers, diluents or excipients. Examples of excipients are water, gelatin, gum arabicum, lactose, microcrystalline cellulose, starch, sodium starch glycolate, calcium hydrogen phosphate, magnesium stearate, talcum, colloidal silicon dioxide, and the like. Such formulations may also contain other pharmacologically active agents, and conventional additives, such as stabilizers, wetting agents, emulsifiers, flavouring agents, buffers, and the like. Usually, the amount of active compounds is between 0.1-95% by weight of the preparation, preferably between 0.2-20% by weight in preparations for parenteral use and more preferably between 1-50% by weight in preparations for oral administration.

The formulations can be further prepared by known methods such as granulation, compression, microencapsulation, spray coating, etc. The formulations may be prepared by conventional methods in the dosage form of tablets, capsules, granules, powders, syrups, suspensions, suppositories or injections. Liquid formulations may be prepared by dissolving or suspending the active substance in water or other suitable vehicles. Tablets and granules may be coated in a conventional manner. To maintain therapeutically effective plasma concentrations for extended periods of time, compounds of the invention may be incorporated into slow release formulations.

The dose level and frequency of dosage of the specific compound will vary depending on a variety of factors including the potency of the specific compound employed, the metabolic stability and length of action of that compound, the patient's age, body weight, general health, sex, diet, mode and time of administration, rate of excretion, drug combination, the severity of the condition to be treated, and the patient undergoing therapy. The daily dosage may, for example, range from about 0.001 mg to about 100 mg per kilo of body weight, administered singly or multiply in doses, e.g. from about 0.01 mg to about 25 mg per kilo of body weight each. Normally, such a dosage is given orally but parenteral administration may also be chosen.

Preparation of Compounds of the Invention

The compounds of formula (I) above may be prepared by, or in analogy with, conventional methods. The preparation of intermediates and compounds according to the examples of the present invention may in particular be illuminated by the following Scheme. Definitions of variables in the structures in schemes herein are commensurate with those of corresponding positions in the formulas delineated herein.

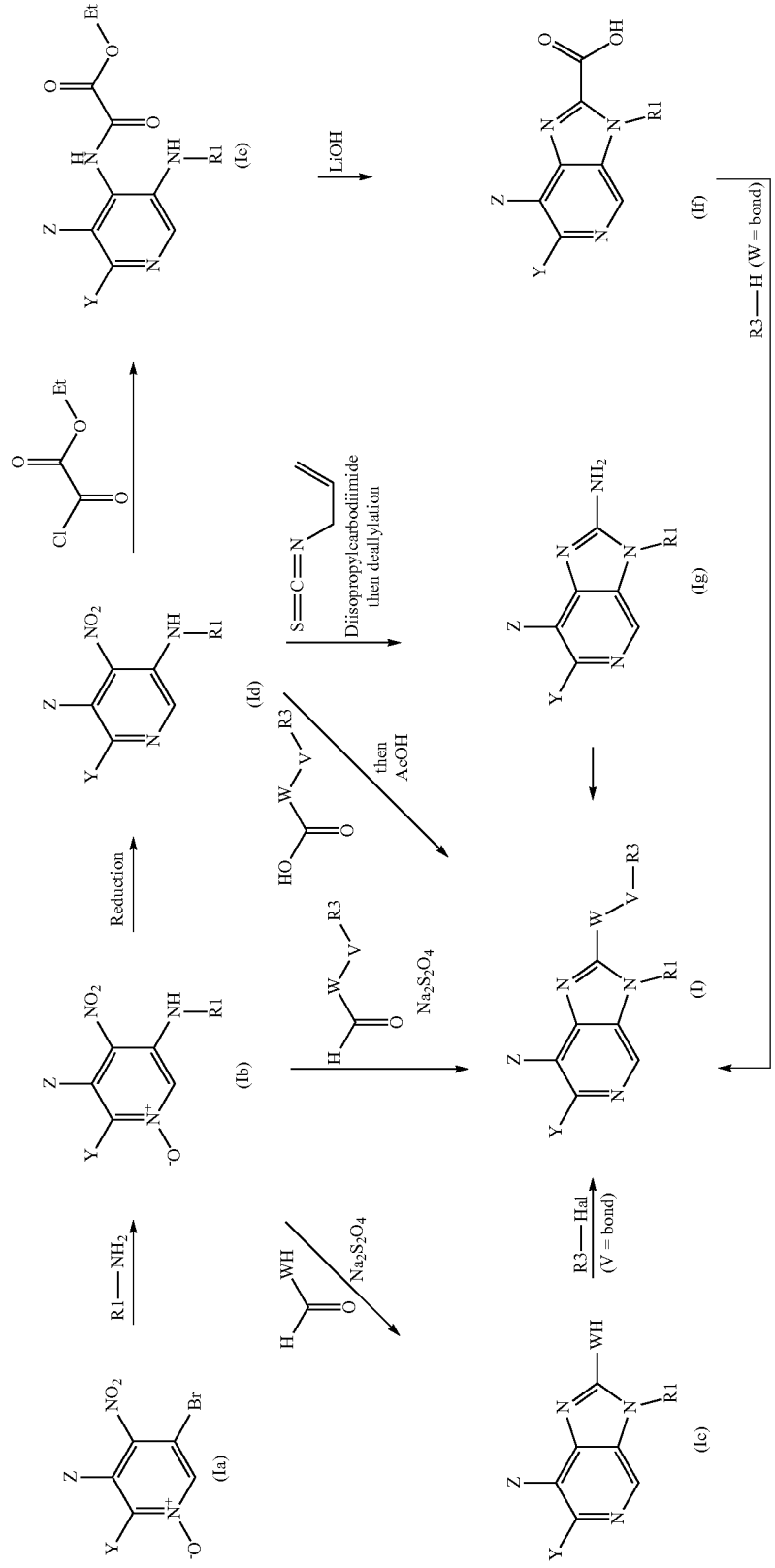

wherein V, W, Y, Z, $R^1$ and $R^3$ are as defined in formula (I);

Compounds of general formula (I) can easily be prepared by standard means. For example, 3-Bromo-4-nitropyridine N-oxides of general formula (Ia) can be treated with aryl or heteroarylamines (R1-$NH_2$) to give intermediates of general formula (Ib) which in turn can be converted to compounds of general formula (I) by reaction with aldehydes H(C=O) WVR3 and $Na_2S_2O_4$ or other suitable conditions. Alternatively, intermediates of general formula (Ib) can be reacted with aldehydes H(C=O)WH (or suitably protected equivalents) and $Na_2S_2O_4$ to give intermediates of general formula (Ic) which in turn can be converted to compounds of general formula (I) by reaction with aryl or heteroaryl halides (Hal=a halogen atom).

Intermediates of general formula (Ib) can also be reduced (for example with, but not limited to, Raney Nickel and ammonium formate, or with iron and acetic acid) to give diamines of general formula (Id). Intermediates of general formula (Id) can be converted to Intermediates of general formula (If) by treatment with ethyl oxalyl chloride and subsequent base induced hydrolysis and cyclisation.

Intermediates of general formula (If) can be converted to compounds of general formula (I) by reaction with for example, amines to produce amides. Alternatively intermediates of general formula (Ig) can be prepared from intermediates of general formula (Id) by cyclisation with allyl isothiocyanate and subsequent deallylation. Amines of general formula (Ig) can be converted to, for example, amides and urethanes of general formula (I) by standard means. Compounds of general formula (I) can also be prepared by coupling of diamines of general formula (Id) with carboxylic acids HO(C=O)WVR3 and subsequent cyclisation for example with acetic acid.

Optionally, the group W—V—R3 can be built up sequentially using standard chemistry. If required, standard protecting group strategies can be employed to facilitate the synthesis. Optionally, a compound of formula (I) can be transformed into another compound of formula (I) in one or more synthetic steps.

The following abbreviations have been used:
Ac acetyl
AcOH acetic acid
Aq aqueous
Ar aryl
nBu n-butyl
Boc tertiary-butyloxycarbonyl
calcd calculated
conc concentrated
d day(s)
DCM dichloromethane
DIPEA diisopropylethylamine
DMA dimethylacetamide
DMF dimethylformamide
DMSO dimethyl sulfoxide
EDC N-(3-dimethylaminopropyl)-N'-ethylcarbodiimide
$ES^+$ electrospray ionization
$Et_3N$ triethylamine
EtOAc ethyl acetate
EtOH ethanol
Ex Example
h hour(s)
HATU O-(7-azabenzotriazol-1-yl)-N,N,N.,N.-tetramethyluronium hexafluorophosphate
HBTU O-benzotriazole-N,N,N',N'-tetramethyl-uronium-hexafluoro phosphate
HOBt hydroxybenzotriazole
HPLC High Performance Liquid Chromatography
HRMS High Resolution Mass Spectrometry
Int Intermediate
LCMS Liquid Chromatography Mass Spectrometry
LDA Lithium diisopropylamide
M molar
MeCN acetonitrile
MeOH methanol
$[MH]^+$ protonated molecular ion
min minute(s)
MS Mass Spectrometry
NMP 1-methyl-2-pyrrolidinone
QTOF Quadrupole time-of-flight mass spectrometer
RP reverse phase
RT room temperature
Rt retention time
sat saturated
TFA trifluoroacetic acid
THF Tetrahydrofuran
UPLC Ultra Performance Liquid Chromatography
UV Ultra violet
XPhos 2-dicyclohexylphosphino-2',4',6'-triisopropylbiphenyl

EXAMPLES AND INTERMEDIATE COMPOUNDS

Experimental Methods

Reactions were conducted at room temperature unless otherwise specified. Microwave reactions were performed with a Biotage microwave reactor using process vials fitted with aluminium caps and septa. Hydrogenations were performed using a Thales H-Cube. Preparative low pressure chromatography was performed using a CombiFlash Companion or Combiflash RF systems equipped with RediSep or GraceResolv silica and C18 reverse phase columns. Preparative reverse phase HPLC was performed on a Gilson system with a UV detector equipped with a ACE-5AQ, 100×21.20 mm, 5 mm or Phenomenex Synergi Hydro-RP 80A AXIA, 100×21.20 mm, 4 mm columns. The purest fractions were collected, concentrated and dried under vacuum. Compounds were typically dried in a vacuum oven between 40° C. and 60° C. prior to purity analysis.

Compound analysis was performed by HPLC and LCMS. The HPLC data was collected using an Agilent 1100 HPLC system with diode array detector and the LCMS data was collected using an Agilent 1100 HPLC system with a Waters ZQ mass spectrometer connected. The standard chromatography method utilised a Phenomenex Synergi RP-Hydro column (150×4.6 mm, 4 μm), a gradient of 5-100% MeCN (+0.085% TFA) in water (+0.1% TFA) over 7 min at 1.5 mL per min and 30° C., with detection at 200-300 nm. Compound analysis was alternatively performed by UPLC using an Agilent UPLC 1290 Infinity system with a Kinetex XB RP column (100×2.1 mm, 1.7 μm), a gradient of 5-100% MeCN (+0.085% TFA) in water (+0.1% TFA) at 0.5 mL per min and 40° C., with detection at 200-300 nm or Kinetex XB RP column (50×2.1 mm, 1.7 μm), a gradient of 5-100% MeCN (+0.085% TFA) in water (+0.1% TFA) at 0.8 mL per min and 40° C., with detection at 200-300 nm.

The standard LCMS method for the intermediates utilised a Phenomenex Synergi RP-Hydro column (30×4.6 mm, 4 μm), a gradient of 5-100% MeCN (+0.085% TFA) in water (+0.1% TFA) over 1.75 min then 100% for 0.75 min at 1.5 mL per min and 30° C., with detection at 200-300 nm). The standard HPLC method for the Intermediates utilised a Zorbax XDB C18 column (50×4.6 mm, 1.8 μm), a gradient of 5-100% MeCN (+0.085% TFA) in water (+0.1% TFA) over 3.0 min then 100% for 0.5 min at 1.2 mL per min and 40° C., with detection at 200-300 nm.

Accurate masses were measured using a Waters QTOF electrospray ion source and corrected using Leucine Enkephalin lockmass. Spectra were acquired in positive and/or negative electrospray mode. The acquired mass range was m/z 100-1000. Test compounds were dissolved in DMSO to give a 10 mM stock solution. Typically 5 uL of the DMSO stock were diluted with 495 uL of acetonitrile and then further diluted with acetonitrile and water (1:1) to give a final concentration of 2 uM. The mass values reported correspond either to the parent molecule with a hydrogen added [MH] or with a hydrogen subtracted [M−H]. The compounds prepared were named using IUPAC.

Intermediate 1

3-[(4-Chlorophenyl)amino]-4-nitropyridin-1-ium-1-olate

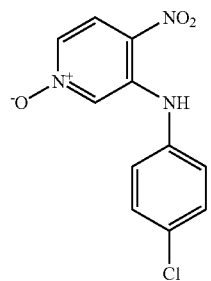

3-Bromo-4-nitropyridine N-oxide (15.0 g, 68.5 mmol) and 4-chloroaniline (26.2 g, 205 mmol) were dissolved in EtOH (100 mL) and heated to 60° C. for 18 h. The reaction mixture was cooled in an ice/water bath and the precipitate was collected by filtration and slurried in EtOH (80 mL) at 60° C. for 2 h to give the title compound as an orange solid (5.68 g, 31.2%). LCMS (ES$^+$): 266.0 [M+H]$^+$. HPLC: Rt 5.45 min, 98.3% purity.

Intermediate 2

3-[(4-Fluorophenyl)amino]-4-nitropyridin-1-ium-1-olate

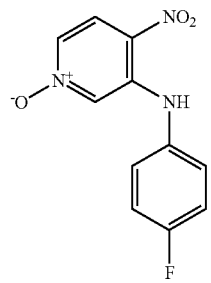

Intermediate 2 was prepared similarly to Intermediate 1, using 4-fluoroaniline instead of 4-chloroaniline, to give the title compound (11.6 g, 40.9%) as an orange solid. LCMS (ES$^+$): 250.0 [MH]$^+$. HPLC: Rt 4.99 min, 100% purity.

Intermediate 3

3-[(4-Methylphenyl)amino]-4-nitropyridin-1-ium-1-olate

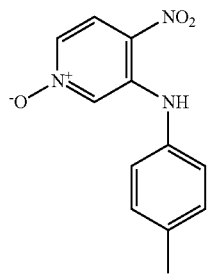

A mixture of 3-fluoro-4-nitropyridne N-oxide (3.25 g, 20.6 mmol) and p-toluidene (5.07 g, 47.3 mmol) in EtOH (100 mL) was stirred for 16 h. The precipitate was isolated by vacuum filtration to give the title product (4.99 g, 98.9%) as an orange solid. LCMS (ES$^+$): 246.1 [M+H]$^+$. HPLC: Rt: 5.61 min, 100% purity.

Intermediate 4

3-N-(4-chlorophenyl)pyridine-3,4-diamine

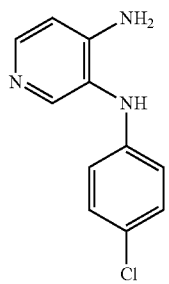 [SMILES: Nc1ccncc1Nc1ccc(Cl)cc1]

Intermediate 1 (457 mg, 1.72 mmol) was dissolved in AcOH (15 mL) and treated with iron powder (480 mg, 8.60 mmol). The reaction mixture was heated at reflux for 1 h then poured into water (100 mL), basified with Na$_2$CO$_3$ and extracted with DCM (3×100 mL). The combined organic layers were dried (MgSO$_4$) and the solvents were removed in vacuo to leave the title compound as a red gum (302 mg, 80.0%). LCMS (ES$^+$): 220.1 [MH]$^+$.

Intermediate 5

3-N-(4-Fluorophenyl)pyridine-3,4-diamine

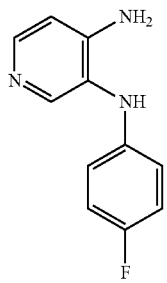 [SMILES: Nc1ccncc1Nc1ccc(F)cc1]

Intermediate 2 (7.77 g, 31.2 mmol) and NH₄HCO₂ (15.7 g, 249 mmol) were suspended in EtOH (250 mL) and Raney nickel (50% in water, 10 mL) was added. The reaction mixture was heated at 85° C. for 2.5 h then allowed to cool to RT, filtered through Celite and the solvents removed in vacuo. The residue was partitioned between sat aq Na₂CO₃ (1.0M, 200 mL) and EtOAc (200 mL). The aqueous layer was extracted with EtOAc (200 mL), the organic layers combined, dried (MgSO₄) and the solvents removed in vacuo. The residue was purified by column chromatography to give the title compound (5.38 g, 84.9%) as a brown gum. LCMS (ES$^+$): 204.2 [MH]$^+$. HPLC: Rt 3.95 min, 99.3% purity.

Intermediate 6

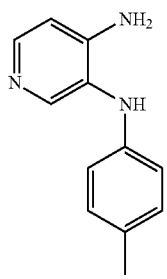

Intermediate 6 was prepared similarly to Intermediate 5 using Intermediate 3 instead of Intermediate 2 to give the title compound (5.01 g, 87.7%) as a pale blue solid. LCMS (ES$^+$): 200.1 [MH]$^+$. HPLC Rt 4.35 min, 100% purity.

Intermediate 7

2-[(2-Hydroxy-2-methylpropyl)amino]pyrimidine-5-carboxylic acid

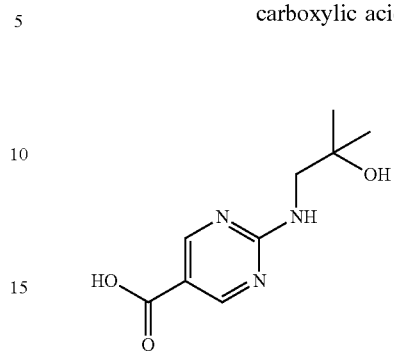

A suspension of 2-chloropyrimidine-5-carboxylic acid (1.00 g, 6.31 mmol), 1-amino-2-methylpropan-2-ol (374 uL, 6.94 mmol) and NEt₃ (1.93 mL, 13.9 mmol) in dioxane (20 mL) was stirred at 100° C. for 2 h. The precipitate was removed by vacuum filtration and the filtrate concentrated in vacuo to give the title compound as a pale pink solid (1.30 g, 97.4%). LCMS (ES$^+$): 194.1 [MH-H₂O]$^+$. UPLC: Rt: 1.30 min, 74.3% purity.

Intermediate 8

N-{3-[(4-Fluorophenyl)amino]pyridin-4-yl}-2-oxo-2,3-dihydro-1H-indole-5-carboxamide

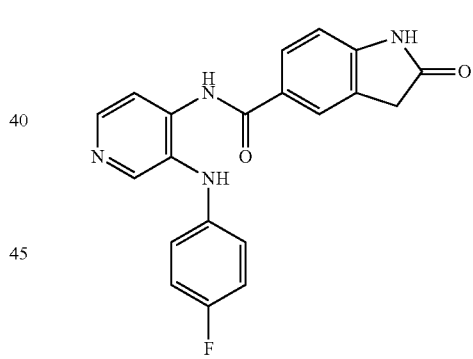

2-Oxo-2,3-dihydro-1H-indole-5-carboxylic acid (200 mg, 1.13 mmol), Intermediate 5 (241 mg, 1.19 mmol), HATU (644 mg, 1.69 mmol) and NEt₃ (392 uL, 2.82 mmol) were dissolved in DMF (7.0 mL) and the reaction mixture heated at 60° C. for 2 h. The reaction mixture was concentrated in vacuo, dissolved in EtOAc (50 mL), washed with water (40 mL). Brine (40 mL) was added to the organic phase and the biphasic mixture was filtered to give the title compound (409 mg, 100%) as a brown solid. LCMS (ES$^+$): 363.1 [MH]$^+$. HPLC: Rt 4.23 min, 79.8% purity.

Intermediates 9-11

Intermediates 9-11 were prepared similarly to Intermediate 8, by coupling of Intermediates 5-6 with the appropriate carboxylic acid; see Table 1 below.

TABLE 1

Amide couplings

| Int | Structure | Name | Intermediate(s), Form, Yield, LCMS, HPLC |
|---|---|---|---|
| 9 | 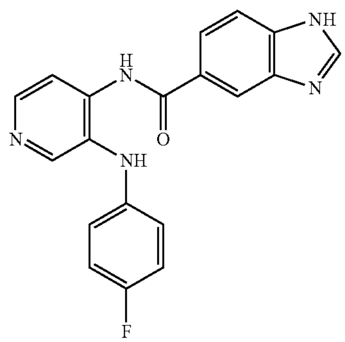 [SMILES: O=C(Nc1ccncc1Nc1ccc(F)cc1)c1ccc2[nH]cnc2c1] | N-{3-[(4-Fluorophenyl)amino]pyridin-4-yl}-1H-1,3-benzodiazole-5-carboxamide | From Intermediate 5<br>Brown solid<br>Yield 300 mg, 70.0%<br>LCMS (ES⁺): 348.1 [MH]⁺ |
| 10 | 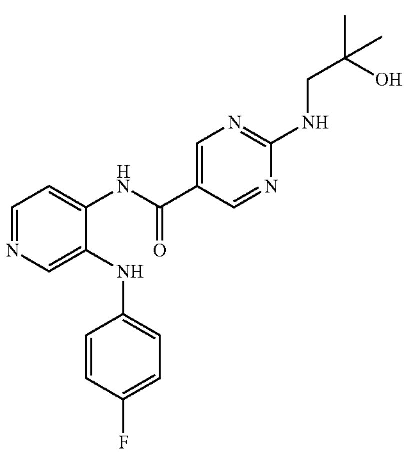 [SMILES: CC(C)(O)CNc1ncc(C(=O)Nc2ccncc2Nc2ccc(F)cc2)cn1] | N-{3-[(4-Fluorophenyl)amino]pyridin-4-yl}-2-[(2-hydroxy-2-methylpropyl)amino]pyrimidine-5-carboxamide | From Intermediates 5 and 7<br>Orange gum<br>Yield 488 mg, crude<br>LCMS (ES⁺): 397.1 [MH]⁺ |
| 11 | 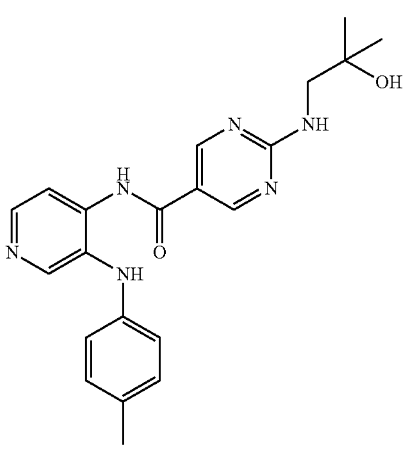 [SMILES: Cc1ccc(Nc2cnccc2NC(=O)c2cnc(NCC(C)(C)O)nc2)cc1] | 2-[(2-Hydroxy-2-methylpropyl)amino]-N-{3-[(4-methylphenyl)amino]pyridin-4-yl}pyrimidine-5-carboxamide | From Intermediates 6 and 7<br>Orange gum<br>Yield 492 mg, crude<br>LCMS (ES⁺): 393.1 [MH]⁺ |

Intermediate 12

Ethyl ({3-[(4-fluorophenyl)amino]pyridin-4-yl}carbamoyl)formate

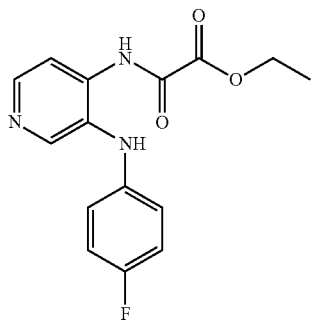 [SMILES: CCOC(=O)C(=O)Nc1ccncc1Nc1ccc(F)cc1]

Intermediate 5 (300 mg, 1.48 mmol) and DIPEA (283 uL, 1.62 mmol) were dissolved in DCM (20 mL). Ethyl oxalyl chloride (173 uL, 1.55 mmol) was added and the reaction mixture stirred for 1 h. The reaction mixture was diluted with DCM (30 mL), washed sat aq NaHCO$_3$ (40 mL), dried (MgSO$_4$) and the solvents removed in vacuo to give the title compound (448 mg, 100%) as a brown gum. LCMS (ES$^+$): 304.1 [MH]$^+$.

Intermediate 13 tert-Butyl 4-[3-(4-chlorophenyl)-3H-imidazo[4,5-c]pyridin-2-yl]piperidine-1-carboxylate

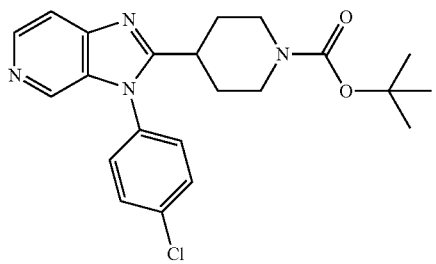 [SMILES: CC(C)(C)OC(=O)N1CCC(c2nc3ccncc3n2-c2ccc(Cl)cc2)CC1]

Intermediate 1 (1.50 g, 5.65 mmol) and 1-Boc-piperidine-4-carbaldehyde (3.61 g, 16.9 mmol) were dissolved in EtOH (20 mL) and treated with Na$_2$S$_2$O$_4$ (3.93 g, 22.6 mmol). The reaction mixture was heated at 140° C. in a microwave reactor for 45 min then poured into 1M aq Na$_2$CO$_3$ (100 mL) and extracted with DCM (3×100 mL). The combined organic layers were dried (MgSO$_4$) and the solvents were removed in vacuo. The residue was purified by column chromatography to give the title compound as a red solid (1.00 g, 42.9%). LCMS (ES$^+$): 413.1 [MH]$^+$. HPLC: Rt 5.45 min, 91.5% purity.

Intermediate 14

4-[3-(4-Chlorophenyl)-3H-imidazo[4,5-c]pyridin-2-yl]piperidine

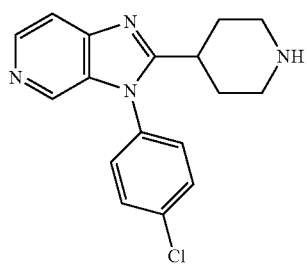 [SMILES: Clc1ccc(-n2c(C3CCNCC3)nc3ccncc32)cc1]

Intermediate 13 (1.00 g, 2.42 mmol) was dissolved in DCM (50 mL) and treated with TFA (10 mL). The reaction mixture was stirred for 18 h, then the solvents were removed in vacuo and the residue was dissolved in 1M aq Na$_2$CO$_3$ (50 mL) and extracted with DCM (3×50 mL). The combined organic layers were dried (MgSO$_4$) and concentrated in vacuo. The residue was purified by column chromatography to give the title compound as a white solid (437 mg, 57.7%). LCMS (ES$^+$): 313.1 [MH]$^+$. HPLC: Rt 3.25 min, 100% purity.

Intermediate 15

3-(4-Fluorophenyl)-3H-imidazo[4,5-c]pyridine-2-carboxylic acid

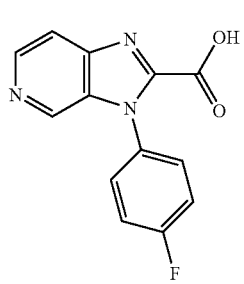 [SMILES: O=C(O)c1nc2ccncc2n1-c1ccc(F)cc1]

Intermediate 12 (448 mg, 1.48 mmol) and LiOH.H$_2$O (65.1 mg, 1.55 mmol) were dissolved in THF (15 mL) and water (10 mL) and the reaction mixture stirred for 2 h. Aqueous HCl (1.0 mL, 1M) was added and stirred for 10 min and the solvents removed in vacuo to give the title compound (380 mg, crude) as a brown solid. LCMS (ES$^+$): 258.0 [MH]$^+$. HPLC: Rt 3.05 min, 91.1% purity.

Example 1

5-[3-(4-Fluorophenyl)-3H-imidazo[4,5-c]pyridin-2-yl]-2,3-dihydro-1H-indol-2-one

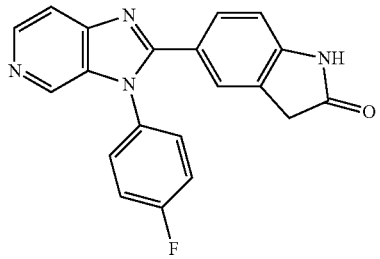 [SMILES: O=C1Cc2cc(-c3nc4ccncc4n3-c3ccc(F)cc3)ccc2N1]

Intermediate 8 (409 mg, 1.13 mmol) was dissolved in AcOH (5 mL) and heated at 110° C. in a microwave reactor for 45 min. The solvents were removed in vacuo and the residue was dissolved in sat aq $NaHCO_3$ (50 mL) and extracted with DCM (50 mL), dried ($MgSO_4$) and the solvents were removed in vacuo. The residue was purified by reverse phase HPLC to yield the title compound (44.0 mg, 11.3%) as a white solid. HRMS ($ES^+$) calculated for [M+H] of $C_{20}H_{13}FN_4O$: 345.1151, found 345.1148. HPLC: Rt 3.87 min, 99.7% purity.

Examples 2-4

Examples 2-4 were prepared similarly to Example 1, by acid mediated cyclisation of Intermediates 9-11; see Table 2 below.

TABLE 2

Cyclisation of Intermediates 8-11

| Ex | Structure | Name | Intermediate(s) used, Form, Yield, LCMS, HPLC |
|---|---|---|---|
| 2 | 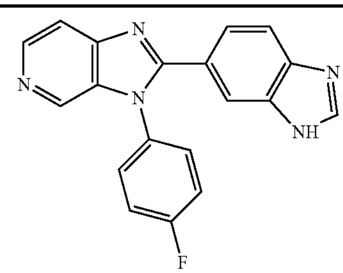 | 5-[3-(4-Fluorophenyl)-3H-imidazo[4,5-c]pyridin-2-yl]-1H-1,3-benzodiazole | From Intermediate 9<br>Cream solid<br>Yield 28.8 mg, 10.1%<br>HRMS ($ES^+$) calculated for [M + H] of $C_{19}H_{12}FN_5$: 330.1155, found 330.1148.<br>HPLC: Rt 3.23 min, 99.8% purity |
| 3 | 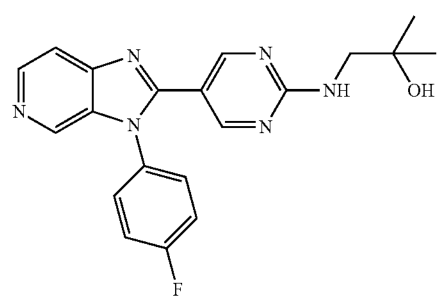 [SMILES: CC(C)(O)CNc1ncc(-c2nc3ccncc3n2-c2ccc(F)cc2)cn1] | 1-({5-[3-(4-Fluorophenyl)-3H-imidazo[4,5-c]pyridin-2-yl]pyrimidin-2-yl}amino)-2-methylpropan-2-ol | From Intermediate 10<br>Off white solid<br>Yield 47.0 mg, 10.1%<br>HRMS ($ES^+$) calculated for [M + H] of $C_{20}H_{19}FN_6O$: 379.1682, found 379.1682.<br>UPLC: Rt 1.90 min, 98.5% purity |
| 4 | 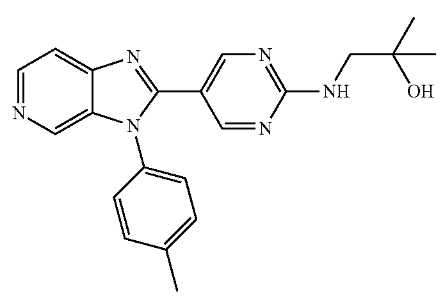 [SMILES: Cc1ccc(-n2c(-c3cnc(NCC(C)(C)O)nc3)nc3ccncc32)cc1] | 2-Methyl-1-({5-[3-(4-methylphenyl)-3H-imidazo[4,5-c]pyridin-2-yl]pyrimidin-2-yl}amino)propan-2-ol | From Intermediate 11<br>Off white solid<br>Yield 21.0 mg, 4.47%<br>HRMS ($ES^+$) calculated for [M + H] of $C_{21}H_{22}N_6O$: 375.1933, found 375.1931.<br>UPLC: Rt 1.99 min, 100% purity |

Example 5

4-{4-[3-(4-Chlorophenyl)-3H-imidazo[4,5-c]pyridin-2-yl]piperidin-1-yl}pyridine; bis(formic acid)

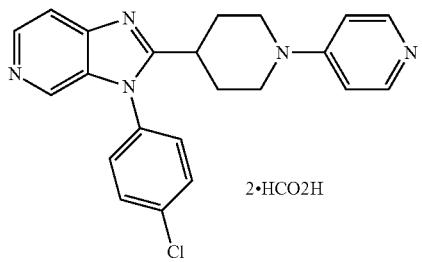 [SMILES: Clc1ccc(-n2c(C3CCN(c4ccncc4)CC3)nc3ccncc32)cc1]

2•HCO2H

Intermediate 14 (200 mg, 0.64 mmol), 4-chloropyridine hydrochloride (192 mg, 1.28 mmol) and DIPEA (445 uL, 2.56 mmol) were dissolved in DMA (3.0 mL) and heated in a microwave reactor at 100° C. for 30 min then at 120° C. for 2.5 h. The solvents were removed in vacuo and the residue was dissolved in 1M aq $Na_2CO_3$ (50 mL) and extracted with DCM (3×50 mL). The combined organic layers were dried ($MgSO_4$) and the solvents were removed in vacuo. The residue was purified reverse phase HPLC to give the title compound as a white solid (50.2 mg, 16.3%). HRMS (ES$^+$) calculated for [M+H] of $C_{22}H_{20}ClN_5$: 390.1485, found 390.1490. HPLC: Rt 4.04 min, 99.4% purity.

Example 6

6-{4-[3-(4-Chlorophenyl)-3H-imidazo[4,5-c]pyridin-2-yl]piperidin-1-yl}-3,4-dihydropyrimidin-4-one

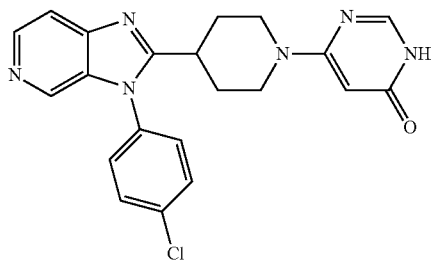 [SMILES: O=c1cc(N2CCC(c3nc4ccncc4n3-c3ccc(Cl)cc3)CC2)nc[nH]1]

Example 6 was prepared similarly to Example 5, using 4-chloro-6-hydroxypyrimidine instead of 4-chloropyridine hydrochloride, to give the title compound (62.0 mg, 23.8%) as a white solid. HRMS (ES$^+$) calculated for [M+H] of $C_{21}H_{19}ClN_6O$: 407.1387, found 407.1383. HPLC: Rt 4.44 min, 99.5% purity.

Example 7

3-{[3-(4-Chlorophenyl)-3H-imidazo[4,5-c]pyridin-2-yl]methyl}pyridine; bis(formic acid)

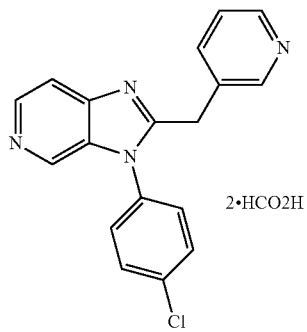 [SMILES: Clc1ccc(-n2c(Cc3cccnc3)nc3ccncc32)cc1]

2•HCO2H

Intermediate 4 (300 mg, 1.37 mmol) and 3-pyridylacetic acid hydrochloride (308 mg, 1.78 mmol) were suspended in polyphosphoric acid (2.0 mL) and heated in a microwave reactor at 180° C. for 1 h. The reaction mixture was dissolved in water (50 mL) and basified with $Na_2CO_3$, then extracted with DCM (3×50 mL). The combined organic layers were dried ($MgSO_4$) and the solvents were removed in vacuo. The residue was purified by reverse phase HPLC to give the title compound as a white solid (35.1 mg, 6.2%). HRMS (ES$^+$) calculated for [M+H] of $C_{18}H_{13}ClN_4$: 321.0907, found 321.0903. HPLC: Rt 3.49 min, 100% purity.

Example 8

1-{3-[3-(4-chlorophenyl)-3H-imidazo[4,5-c]pyridin-2-yl]propyl}-1H-imidazole

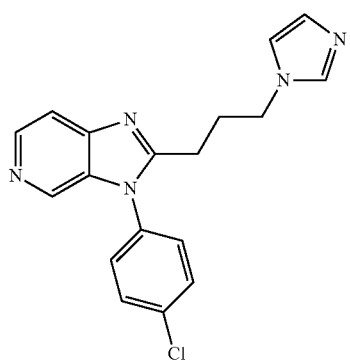 [SMILES: Clc1ccc(-n2c(CCCn3ccnc3)nc3ccncc32)cc1]

Example 8 was prepared similarly to Example 7, using 4-imidazol-1-ylbutyric acid instead of 3-pyridylacetic acid hydrochloride, to give the title compound (68.0 mg, 14.7%) as a yellow gum. HRMS (ES$^+$) calculated for [M+H] of $C_{18}H_{16}ClN_5$: 338.1172, found 338.1167. HPLC: Rt 3.54 min, 98.9% purity.

Example 9

3-(4-Fluorophenyl)-N-(oxan-4-ylmethyl)-3H-imidazo[4,5-c]pyridine-2-carboxamide

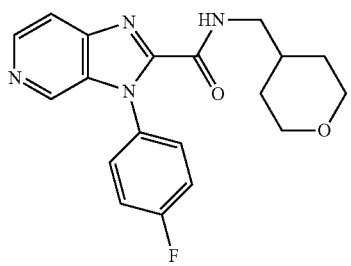 [SMILES: O=C(NCC1CCOCC1)c1nc2ccncc2n1-c1ccc(F)cc1]

Intermediate 15 (190 mg, 0.74 mmol), 4-aminomethyl-tetrahydropyran (89.3 mg, 0.78 mmol), HATU (421 mg, 1.11 mmol) and NEt$_3$ (257 uL, 1.85 mmol) were dissolved in DMF (10 mL) and the reaction mixture stirred for 18 h. The solvents were removed in vacuo. The residue was suspended in sat aq NaHCO$_3$ (40 mL), extracted with EtOAc (2×50 mL), dried (MgSO$_4$) and the solvents removed in vacuo. The residue was purified by column chromatography and by reverse phase HPLC to give the title compound (22.8 mg, 8.70%) as an off white solid. HRMS (ES$^+$) calculated for [M+H] of C$_{19}$H$_{19}$FN$_4$O$_2$: 355.1570, found 355.1568. HPLC: Rt 4.24 min, 97.2% purity.

Biological Tests

Biological Assays of the SSAO Enzyme Inhibitors

All primary assays were performed at RT. with purified recombinantly expressed human SSAO. Enzyme was prepared essentially as described in Öhman et al. (*Protein Expression and Purification* 46 (2006) 321-331). In addition, secondary- and selectivity assays were performed using SSAO prepared from various tissues or purified rat recombinant SSAO. The enzyme activity was assayed with benzylamine as substrate by measuring either benzaldehyde production, using $^{14}$C-labeled substrate, or by utilizing the production of hydrogen peroxide in a horseradish peroxidase (HRP) coupled reaction. Briefly, test compounds were dissolved in dimethyl sulfoxide (DMSO) to a concentration of 10 mM. Dose-response measurements were assayed by either creating 1:10 serial dilutions in DMSO to produce a 7 point curve or by making 1:3 serial dilutions in DMSO to produce 11 point curves. The top concentrations were adjusted depending on the potency of the compounds and subsequent dilution in reaction buffer yielded a final DMSO concentration ≤2%.

Hydrogen Peroxide Detection:

In a horseradish peroxidase (HRP) coupled reaction, hydrogen peroxide oxidation of 10-acetyl-3,7-dihydroxyphenoxazine produced resorufin, which is a highly fluorescent compound (Zhout and Panchuk-Voloshina. Analytical Biochemistry 253 (1997) 169-174; Amplex® Red Hydrogen Peroxide/peroxidase Assay kit, Invitrogen A22188). Enzyme and compounds in 50 mM sodium phosphate, pH 7.4 were set to pre-incubate in flat-bottomed microtiter plates for approximately 15 min before initiating the reaction by addition of a mixture of HRP, benzylamine and Amplex reagent. Benzylamine concentration was fixed at a concentration corresponding to the Michaelis constant, determined using standard procedures. Fluorescence intensity was then measured at several time points during 1-2 h, exciting at 544 nm and reading the emission at 590 nm. For the human SSAO assay final concentrations of the reagents in the assay wells were: SSAO enzyme 1 ug/mL, benzylamine 100 uM, Amplex reagent 20 uM, HRP 0.1 U/mL and varying concentrations of test compound. The inhibition was measured as % decrease of the signal compared to a control without inhibitor (only diluted DMSO). The background signal from a sample containing no SSAO enzyme was subtracted from all data points. Data was fitted to a four parameter logistic model and IC$_{50}$ values were calculated using the GraphPad Prism 4 or XLfit 4 programs.

Aldehyde Detection:

SSAO activity was assayed using 14C-labeled benzylamine and analysed by measuring radioactive benzaldehyde. In a white 96-well optiplate (Packard), 20 uL of diluted test compound was pre-incubated at RT with 20 uL SSAO enzyme for approximately 15 min with continuous agitation. All dilutions were made with PBS. The reaction was initiated by adding 20 uL of the benzylamine substrate solution containing [7-14C] Benzylamine hydrochloride (CFA589, GE Healthcare). The plate was incubated for 1 h as above after which the reaction was stopped by acidification (10 uL 1M aq HCl). Then 90 uL Micro Scint-E solution (Perkin-Elmer) was added to each well and the plate was continuously mixed for 15 min. Phase separation occurred instantly and activity was read in a Topcount scintillation counter (Perkin-Elmer). In the final reaction well, the human recombinant SSAO concentration was 10 ug/mL. In order to optimize sensitivity, the substrate concentration was decreased as compared to the HRP coupled assay in order to get a higher fraction of radioactive product. In the human SSAO assay, benzylamine concentration was 40 uM (0.2 uCi/mL). Data was analysed as above.

All of the exemplified compounds of the invention had an IC$_{50}$ value of between 1 nM and 500 nM at SSAO (see Table 3 below).

TABLE 3

| Compound | SSAO inhibitory activity (A: <50 nM, B: 50-200 nM, C: 200-500 nM) SSAO IC$_{50}$ (nM) |
|---|---|
| 1 | B |
| 2 | C |
| 3 | A |
| 4 | A |
| 5 | A |
| 6 | C |
| 7 | C |
| 8 | C |
| 9 | C | hERG Assay

Compounds of the invention were tested for inhibition of the human ether a go-go related gene (hERG) K$^+$ channel using IonWorks patch clamp electrophysiology. 8 Point concentration-response curves were generated on two occasions using 3-fold serial dilutions from the maximum assay concentration (11 uM). Electrophysiological recordings were made from a Chinese Hamster Lung cell line stably expressing the full length hERG channel. Single cell ion currents were measured in the perforated patch clamp configuration (100 ug/mL amphoterocin) at RT using an IonWorks Quattro instrument. The internal solution contained 140 mM KCl, 1 mM MgCl$_2$, 1 mM EGTA and 20 mM HEPES and was buffered to pH 7.3. The external solution contained 138 mM NaCl, 2.7 mM KCl, 0.9 mM CaCl$_2$, 0.5 mM MgCl$_2$, 8 mM Na$_2$HPO$_4$ and 1.5 mM KH$_2$PO$_4$, and was buffered to pH 7.3. Cells were clamped at a holding potential of 70 mV for 30 s and then stepped to +40 mV for 1 s. This was followed by a hyperpolarising step of 1 s to 30 mV to evoke the hERG tail current. This sequence was repeated 5 times at a frequency of 0.25 Hz. Currents were measured from the tail step at the 5$^{th}$ pulse, and referenced to the holding current. Compounds were incubated for 6-7 min prior to a second measurement of the hERG signal using an identical pulse train. A minimum of 17 cells were required for each pIC50 curve fit. A control compound (quinidine) was used (see Table 4 below).

TABLE 4

| hERG IC50 (A: >10 uM, B: 1-10 uM, C: 0.01M-1 uM) | |
|---|---|
| Compound | hERG IC50 |
| 3 | A |
| 5 | C |

The invention claimed is:

1. A compound of formula (I) or a pharmaceutically acceptable salt, or N-oxide thereof:

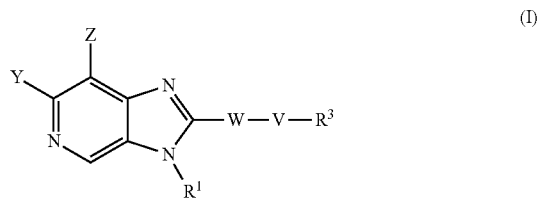

(I)

wherein Y is selected from hydrogen, hydroxyl, —NH$_2$, —NH—C$_{1-4}$-alkyl, —NH-halo-C$_{1-4}$-alkyl, or —C$_{1-4}$-alkoxy;
wherein Z is selected from hydrogen, halogen, hydroxyl, cyano, C$_{1-4}$-alkyl, halo-C$_{1-4}$-alkyl, C$_{1-4}$-alkoxy, halo-C$_{1-4}$-alkoxy, —CONH$_2$, —SO$_2$NH$_2$, —NH$_2$, —NHC$_{1-4}$-alkyl, and —NH-halo-C$_{1-4}$-alkyl;
wherein R$^1$ is a phenyl ring, or a 5 or 6-membered heteroaryl ring, either ring optionally substituted with one or more substituents selected from halogen, cyano, C$_{1-4}$-alkyl, halo-C$_{1-4}$-alkyl, cyano-C$_{1-4}$-alkyl, —OR$^5$, NR$^{4A}$R$^{4B}$, —NR$^6$C(O)OR$^5$, —NR$^6$C(O)R$^5$, —NR$^6$C(O)NR$^{4A}$R$^{4B}$, —C(O)NR$^{4A}$R$^{4B}$, —C(O)R$^5$, —C(O)OR$^5$, and —NR$^6$S(O)$_2$R$^5$;
  wherein R$^{4A}$, R$^{4B}$, R$^5$, and R$^6$ are each independently selected from hydrogen, C$_{1-4}$-alkyl and halo-C$_{1-4}$-alkyl, or
  wherein each of R$^{4A}$ and R$^{4B}$, together with the nitrogen to which they are attached, form a 3-7 membered cyclic amino group, optionally substituted by one or more substituents selected from: halogen, hydroxyl, cyano, C$_{1-4}$-alkyl, halo-C$_{1-4}$-alkyl, C$_{1-4}$-alkoxy, halo-C$_{1-4}$-alkoxy, —CONH$_2$, —SO$_2$NH$_2$, —NH$_2$, —NHC$_{1-4}$-alkyl, and —NH-halo-C$_{1-4}$-alkyl;
wherein W is a [6,5] heteroaryl ring system formed by fusing together phenyl and pyrrolidinyl or imidazolyl and wherein either ring is optionally substituted with one or more groups selected from halogen, oxo, hydroxyl, cyano, C$_{1-4}$-alkyl, halo-C$_{1-4}$-alkyl, cyano-C$_{1-4}$-alkyl, —OR$^5$, —NR$^{4A}$R$^{4B}$, —NR$^6$C(O)OR$^5$, —NR$^6$C(O)R$^5$, —NR$^6$C(O)NR$^{4A}$R$^{4B}$, —C(O)NR$^{4A}$R$^{4B}$, —C(O)R$^5$, —C(O)OR$^5$, —SO$_2$R$^5$, —SO$_2$NR$^{4A}$R$^{4B}$, and —NR$^6$S(O)$_2$R$^5$;
wherein V is a direct bond; and
wherein R$^3$ is hydrogen.

2. The compound according to claim 1, wherein W has the formula A1 or A2:

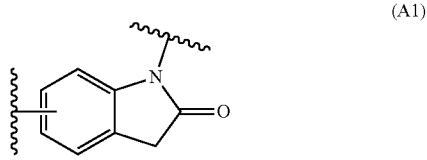

(A1)

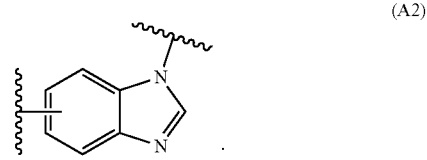

(A2)

3. A method for the treatment of inflammation, which comprises administering to a subject suffering such disease an effective amount of a compound according to claim 1.

4. A compound of formula (I) or a pharmaceutically acceptable salt, or N-oxide thereof:

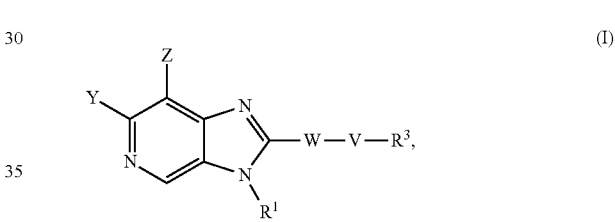

(I)

wherein Y is selected from hydrogen, hydroxyl, —NH$_2$, —NH—C$_{1-4}$-alkyl, —NH-halo-C$_{1-4}$-alkyl, and —C$_{1-4}$-alkoxy;
wherein Z is selected from hydrogen, halogen, hydroxyl, cyano, C$_{1-4}$-alkyl, halo-C$_{1-4}$-alkyl, C$_{1-4}$-alkoxy, halo-C$_{1-4}$-alkoxy, —CONH$_2$, —SO$_2$NH$_2$, —NH$_2$, —NHC$_{1-4}$-alkyl, and —NH-halo-C$_{1-4}$-alkyl;
wherein R$^1$ is a phenyl ring, or a 5 or 6-membered heteroaryl ring, either ring optionally substituted with one or more substituents selected from halogen, cyano, C$_{1-4}$-alkyl, halo-C$_{1-4}$-alkyl, cyano-C$_{1-4}$-alkyl, —OR$^5$, —NR$^{4A}$R$^{4B}$, —NR$^6$C(O)OR$^5$, —NR$^6$C(O)R$^5$, —NR$^6$C(O)NR$^{4A}$R$^{4B}$, —C(O)NR$^{4A}$R$^{4B}$, —C(O)R$^5$, —C(O)OR$^5$, and —NR$^6$S(O)$_2$R$^5$;
  wherein R$^{4A}$, R$^{4B}$, R$^5$, and R$^6$ are each independently selected from hydrogen, C$_{1-4}$-alkyl and halo-C$_{1-4}$-alkyl, or
  wherein each of R$^{4A}$ and R$^{4B}$, together with the nitrogen to which they are attached, form a 3-7 membered cyclic amino group, optionally substituted by one or more substituents selected from: halogen, hydroxyl, cyano, C$_{1-4}$-alkyl, halo-C$_{1-4}$-alkyl, C$_{1-4}$-alkoxy, halo-C$_{1-4}$-alkoxy, —CONH$_2$, —SO$_2$NH$_2$, —NH$_2$, —NHC$_{1-4}$-alkyl, and —NH-halo-C$_{1-4}$-alkyl;
wherein W is a 5 or 6-membered heterocyclic ring optionally substituted with one or more substituents selected from halogen, oxo, hydroxyl, cyano, C$_{1-4}$-alkyl, halo-C$_{1-4}$-alkyl, cyano-C$_{1-4}$-alkyl, —OR$^5$, —NR$^{4A}$R$^{4B}$, —NR$^6$C(O)OR$^5$, —NR$^6$C(O)R$^5$, —NR$^6$C(O)

NR⁴ᴬR⁴ᴮ, —C(O)NR⁴ᴬR⁴ᴮ, —C(O)R⁵, —C(O)OR⁵, —SO₂R⁵, —SO₂NR⁴ᴬR⁴ᴮ, and —NR⁶S(O)₂R⁵;

wherein V is a direct bond; and wherein R³ is a phenyl ring or a 5 or 6-membered heteroaryl ring optionally substituted with one or more substituents selected from halogen, oxo, hydroxyl, cyano, C₁₋₄-alkyl, halo-C₁₋₄-alkyl, cyano-C₁₋₄-alkyl, —OR⁵, —NR⁴ᴬR⁴ᴮ, —NR⁶C(O)OR⁵, —NR⁶C(O)R⁵, —NR⁶C(O)NR⁴ᴬR⁴ᴮ, —C(O)NR⁴ᴬR⁴ᴮ, —C(O)R⁵, —C(O)OR⁵, —SO₂R⁵, —SO₂NR⁴ᴬR⁴ᴮ and —NR⁶S(O)₂R⁵.

5. A pharmaceutical composition comprising an effective amount of a compound according to claim 1, and a pharmaceutically acceptable carrier.

6. A method for the treatment of inflammation, which comprises administering to a subject suffering such disease an effective amount of a compound according to claim 4.

7. A pharmaceutical composition comprising an effective amount of a compound according to claim 4, and a pharmaceutically acceptable carrier.

8. The compound according to claim 1, wherein the compound is:

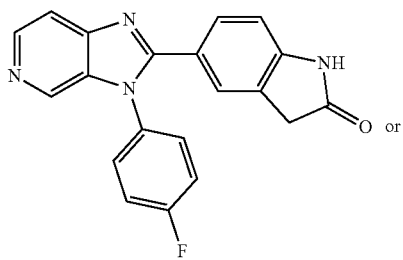

or

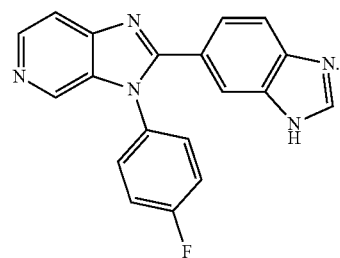

9. The method according to claim 3, wherein the compound is:

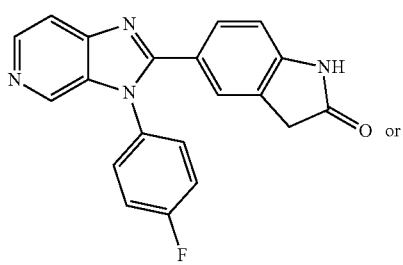

or

10. The compound according to claim 4, wherein the compound is:

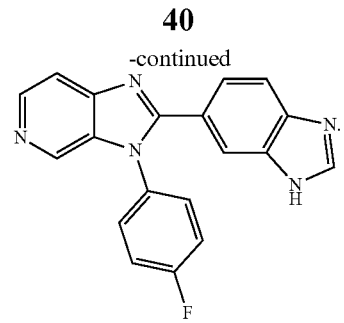

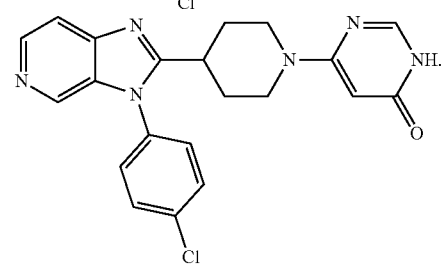

or

11. The method according to claim 6, wherein the compound is:

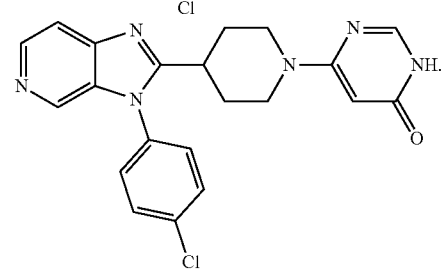

or

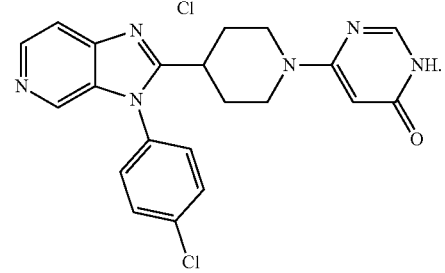

12. The compound according to claim 4, wherein W is a ring selected from piperidine, morpholine, pyrrolidine, and piperazine, any of which is optionally substituted with one or more groups selected from halogen, oxo, hydroxyl, cyano, C₁₋₄-alkyl, halo-C₁₋₄-alkyl, cyano-C₁₋₄-alkyl, —OR⁵, —NR⁴ᴬR⁴ᴮ, —NR⁶C(O)OR⁵, —NR⁶C(O)R⁵, —NR⁶C(O)NR⁴ᴬR⁴ᴮ, —C(O)NR⁴ᴬR⁴ᴮ, —C(O)R⁵, —C(O)OR⁵, —SO₂R⁵, —SO₂NR⁴ᴬR⁴ᴮ, and —NR⁶S(O)₂R⁵.

13. The compound according to claim 12, wherein —WVR³ is:

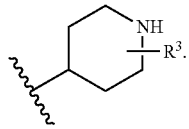

14. The compound according to claim 4, wherein R³ is selected from phenyl, pyridyl, and pyrimidinyl, any of which is optionally substituted with oxo.

15. The compound according to claim 12, wherein R³ is selected from phenyl, pyridyl and pyrimidinyl, any of which is optionally substituted with oxo.

16. The compound according to claim 13, wherein R³ is selected from phenyl, pyridyl and pyrimidinyl, any of which is optionally substituted with oxo.

* * * * *